(12) United States Patent
Johnson, Jr. et al.

(10) Patent No.: US 8,330,605 B2
(45) Date of Patent: Dec. 11, 2012

(54) SYSTEM FOR PROVIDING REAL TIME LOCATING AND GAS EXPOSURE MONITORING

(75) Inventors: Ernest K. Johnson, Jr., Novelty, OH (US); Mark J. Davisson, Rensselaer, IN (US)

(73) Assignee: Accenture Global Services Limited (IE)

( * ) Notice: Subject to any disclaimer, the term of this patent is extended or adjusted under 35 U.S.C. 154(b) by 400 days.

(21) Appl. No.: 12/634,110

(22) Filed: Dec. 9, 2009

(65) Prior Publication Data

US 2011/0037599 A1    Feb. 17, 2011

Related U.S. Application Data

(60) Provisional application No. 61/234,134, filed on Aug. 14, 2009.

(51) Int. Cl.
    *G08B 17/10*    (2006.01)
    *G05B 23/02*    (2006.01)
    *G05B 1/08*    (2006.01)

(52) U.S. Cl. ............... 340/632; 340/3.1; 340/539.13; 340/539.11

(58) Field of Classification Search ............... 340/3.1, 340/632, 539.13, 539.11, 539.1, 539.21, 340/573.1
See application file for complete search history.

(56) References Cited

U.S. PATENT DOCUMENTS

| | | | |
|---|---|---|---|
| 4,665,385 A | 5/1987 | Henderson | |
| 5,568,121 A | 10/1996 | Lamensdorf | |
| 5,771,004 A | 6/1998 | Suppelsa et al. | |
| 6,053,030 A | 4/2000 | Whynall et al. | |
| 6,182,497 B1 | 2/2001 | Krajci | |
| 6,415,646 B1 | 7/2002 | Kessel et al. | |
| 6,670,887 B2 | 12/2003 | Dungan | |
| 6,856,253 B1 | 2/2005 | Crook | |
| 7,071,821 B2 | 7/2006 | Adamczyk et al. | |
| 7,080,544 B2 | 7/2006 | Stepanik et al. | |
| 7,102,517 B2 | 9/2006 | Reyes et al. | |
| 7,126,104 B2 | 10/2006 | Smith et al. | |
| 7,148,803 B2 | 12/2006 | Bandy et al. | |

(Continued)

FOREIGN PATENT DOCUMENTS

CN    2849859 Y    12/2006

(Continued)

OTHER PUBLICATIONS

U.S. Appl. No. 11/668,367, Unpublished.

(Continued)

*Primary Examiner* — Brian Zimmerman
*Assistant Examiner* — Omeed Alizada
(74) *Attorney, Agent, or Firm* — Brinks Hofer Gilson & Lione

(57) ABSTRACT

A system is described for providing real time locating and gas exposure monitoring. The system may include a memory, interface, and processor. The memory may store an alarm data item including an amount of gas exposure and a location identifier. The processor may receive the alarm data item from a sensor device of a first user. The processor may identify a relative location of the first user based on the location identifier. The processor may determine a second user located within a proximity of the first user. The processor may communicate to the second user the relative location of the first user and the gas exposure of the first user. The processor may receive, from the second user, an indication of whether an emergency responder should be contacted. The processor may initiate communication with an emergency responder if the indication indicates an emergency responder should be contacted.

23 Claims, 12 Drawing Sheets

U.S. PATENT DOCUMENTS

| | | | |
|---|---|---|---|
| 7,171,312 | B2 | 1/2007 | Steinthal et al. |
| 7,197,013 | B2 | 3/2007 | Douglas et al. |
| 7,259,656 | B1 | 8/2007 | Wright |
| 7,263,379 | B1 | 8/2007 | Parkulo et al. |
| 7,302,313 | B2 | 11/2007 | Sharp et al. |
| 7,369,945 | B2 | 5/2008 | Miller et al. |
| 7,463,160 | B2 | 12/2008 | Crook |
| 7,515,578 | B2 | 4/2009 | Alizadeh-Shabdiz et al. |
| 7,528,711 | B2 | 5/2009 | Kates |
| 7,663,359 | B2 | 2/2010 | Li et al. |
| 2002/0155622 | A1 | 10/2002 | Slater et al. |
| 2004/0120857 | A1 | 6/2004 | Smith et al. |
| 2004/0236547 | A1 | 11/2004 | Rappaport et al. |
| 2007/0005267 | A1 | 1/2007 | Li |
| 2007/0219645 | A1 | 9/2007 | Thomas et al. |
| 2008/0280565 | A1 | 11/2008 | Jevremovic et al. |
| 2009/0029716 | A1 | 1/2009 | Thomas |
| 2010/0081411 | A1 | 4/2010 | Montenero |

FOREIGN PATENT DOCUMENTS

| | | |
|---|---|---|
| CN | 101216987 A | 7/2008 |
| CN | 101545897 A | 9/2009 |
| CN | 201314243 Y | 9/2009 |
| CN | 201340646 Y | 11/2009 |

OTHER PUBLICATIONS

U.S. Appl. No. 12/121,705, Unpublished.
U.S. Appl. No. 60/890,396, Unpublished.
U.S. Appl. No. 60/941,985, Unpublished.
U.S. Appl. No. 61/023,355, Unpublished.
U.S. Appl. No. 61/057,124, Unpublished.
"LDARtools.com—News around fugitive." <http://www.Idartools.com/News.aspx>. Jul. 22, 2010.
*Gas Detecting and Monitoring Solutions for Life.* vol. 7, No. 1. Industrial Scientific Corporation. 2008. 88 pgs.
"AeroScout T6 GPS Tags." <www.aeroscout.com/content/t6gps>. Aug. 12, 2009.
"AeroScout Mobile View." <www.aeroscout.com/content/mobileview>. Aug. 12, 2009.
"WiFi Tags." <www.airetrak.com/wifi/wifi_tags.php>. Sep. 28, 2009.
"AeroScout T3 Tags." <http://www.aeroscout.com/content/t3>. Aug. 12, 2009.
"AeroScout T5 Sensor Tags." <www.aeroscout.com/content/t5sensor>. Aug. 12, 2009.
"Oil and Gas." <www.aeroscout.com/content/energy>. Aug. 12, 2009.
"Oil and Gas." <http://www.rtls.se/OilGas.aspx>. Sep. 28, 2009.
"Asset Visibility Solutions for Manufacturing and Logistics Real-time location and status throughout your enterprise." AeroScout, Inc. Nov. 2008. 6 pgs.
"Cisco and AeroScout Location-Based Services for Manufacturing." Cisco Systems, Inc. 2006. 4 pgs.
"Cisco Wireless Location Appliance." Cisco Systems, Inc. 2007. 7 pgs.
"iNet—How it works." <www.indsci.com/inethowitworks.aspx>. Aug. 12, 2009.
"iNet—Control." <http://www.indsci.com/inetcontrol.aspx>. Aug. 12, 2009.
inetcontrol._web.jpg. Aug. 12, 2009. 1 pg.
webinetflow.jpg. Aug. 12, 2009. 1 pg.
"GasBadge Pro@ Dockable Single Gas Monitor." Industrial Scientific Corp. Jun. 2007. 2pgs.
"GasBadge Plus@ Personal Single Gas Monitor." Industrial Scientific Corp. Jun. 2007. 2 pgs.
Roseberg P.Eng, Steve. "RFID in the Oilfield Location Based Services for Industrial Environments". *Cisco.* Jun. 5, 2008. 30 pgs.

SYSTEM FOR PROVIDING REAL TIME LOCATING AND GAS EXPOSURE MONITORING

CROSS-REFERENCE TO RELATED APPLICATIONS

This application claims the benefit of U.S. Provisional Application No. 61/234,134, filed on Aug. 14, 2009, which is incorporated by reference herein.

TECHNICAL FIELD

The present description relates generally to a system and method, generally referred to as a system, for providing real time locating and gas exposure monitoring, and more particularly, but not exclusively, to monitoring the location of employees and the exposure of employees to hazardous materials, such as hazardous gases.

BACKGROUND

Individuals working in hazardous environments, such as refineries, chemical plants, or nuclear power plants, may be exposed to hazardous materials, such as hazardous gases, chemical compounds, or radiation. Prolonged exposure to hazardous materials may lead to sickness or death. Thus, each individual entering a hazardous environment may be required to wear a badge containing a sensor which detects the level of exposure of the individual to the hazardous materials. The badge may alert the individual if the individual is being exposed to harmful levels of hazardous materials. When the badge alerts the individual, the individual is expected to vacate the contaminated area containing the hazardous materials, thereby reducing their exposure to the hazardous materials. However, in some instances the individual may not vacate the contaminated area and may continue to be exposed to the hazardous materials for a prolonged period of time. For example, the individual may not notice the alert, or may simply ignore the alert. The prolonged exposure to the hazardous materials may cause the individual to suffer from serious sickness or death.

SUMMARY

A system for providing real time locating and gas exposure monitoring may include a memory, an interface, and a processor. The memory may be connected to the processor and the interface and may store an alarm data item. The alarm data item may include an amount of gas exposure and a location identifier. The interface may be operatively connected to the memory and may communicate with a sensor device of a first user in a work area, a computing device of a second user in the work area, and a communication device of an emergency responder. The processor may be operatively connected to the memory and the interface. The processor may receive, via the interface, the alarm data item from the sensor device of the first user in the work area. The processor may identify a relative location of the first user in the work area based on the location identifier. The processor may determine a second user who is located within a proximity of the first user. The processor may communicate, via the interface to the computing device of the second user, the relative location of the first user and the amount of gas exposure of the first user. The processor may receive, via the interface from the computing device of the second user, an indication of whether an emergency responder should be contacted. The processor may initiate, via the interface, a communication with the communication device of the emergency responder if the indication indicates the emergency responder should be contacted. Otherwise the processor may close the alarm data item.

Other systems, methods, features and advantages will be, or will become, apparent to one with skill in the art upon examination of the following figures and detailed description. It is intended that all such additional systems, methods, features and advantages be included within this description, be within the scope of the embodiments, and be protected by the following claims and be defined by the following claims. Further aspects and advantages are discussed below in conjunction with the description.

BRIEF DESCRIPTION OF THE DRAWINGS

The system and/or method may be better understood with reference to the following drawings and description. Non-limiting and non-exhaustive descriptions are described with reference to the following drawings. The components in the figures are not necessarily to scale, emphasis instead being placed upon illustrating principles. In the figures, like referenced numerals may refer to like parts throughout the different figures unless otherwise specified.

DETAILED DESCRIPTION

A system and method, generally referred to as a system, may relate to providing real time locating and gas exposure monitoring, and more particularly, but not exclusively, monitoring the location of employees and the exposure of employees to hazardous materials, such as hydrogen sulfide. For explanatory purposes, the detailed description discusses monitoring the location of employees and the exposure of employees to hazardous gases. However, in other embodiments the system may be used for monitoring the location of employees and the exposure of employees to any hazardous materials. The principles described herein may be embodied in many different forms.

The system may allow an organization to monitor the location of each individual in a work area, and the level of exposure of each individual to one or more hazardous materials. Each individual entering the area may be provided with a gas detection and real time locating device which communicates the gas exposure and location of the individual to a server. When the gas exposure of the individual meets an alarm threshold, the system performs one or more alarm handling actions, such as locating the individual, initiating communication with the individual, alerting operators in the vicinity of the individual, initiating communication with responders, or generally any actions which may be necessary to respond to the alarm. The gas detection and real time locating device may include a panic button, which, when activated by an individual, communicates an alarm to the server. The gas detection and real time locating device may also detect when an individual fails to move for a period of time. The gas detection and real time locating device may send a local alert to the individual, such as by vibrating. If the individual does not respond to the local alert, the device may send an alarm to the server. The gas detection and real time locating device may also include additional sensors to monitor other stimuli, such as biometric sensors for monitoring heart rate, blood pressure or other health related measures.

The system may allow the organization to quickly locate individuals exposed to harmful levels of hazardous materials and evacuate the individuals from the contaminated area. The system may allow the organization to expand their gas detection network to include each individual carrying a gas detection device in the work area. The expanded gas sensor network may provide the organization with advanced notice of gas leaks or contamination and may allow the organization to quickly evacuate the individuals located in the proximity of the contamination. The system may use a combination of network infrastructure and satellite positioning systems to monitor the location of individuals in an indoor/outdoor work environment.

Figure 1:
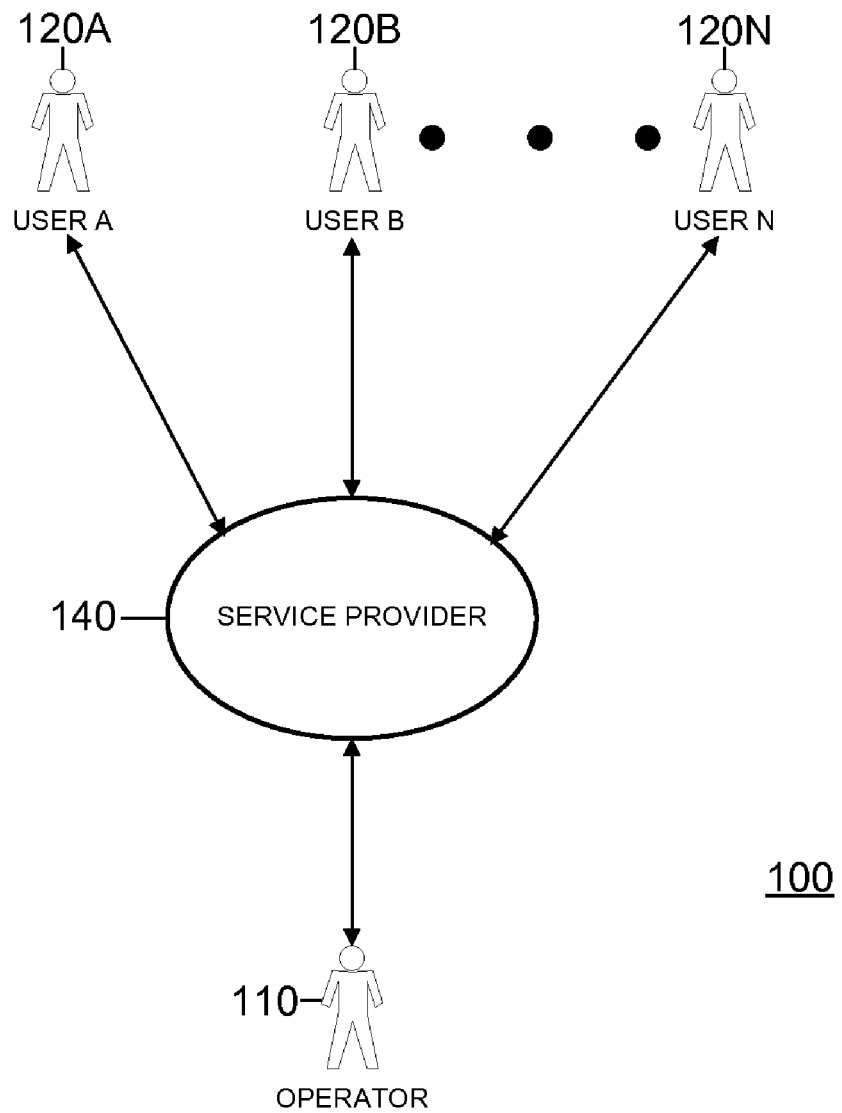
FIG. 1 is a block diagram of a general overview of a system for providing real time locating and gas exposure monitoring.

FIG. 1 provides a general overview of a system 100 for providing real time locating and gas exposure monitoring. Not all of the depicted components may be required, however, and some implementations may include additional components. Variations in the arrangement and type of the components may be made without departing from the spirit or scope of the claims as set forth herein. Additional, different or fewer components may be provided.

The system 100 may include one or more users 120A-N, an operator 110, and a service provider 140. The users 120A-N may be employees of an organization who work in a hazardous work environment, such as a refinery, a nuclear power plant, a chemical plant, a mine, or any other hazardous work environment. The users 120A-N may be exposed to harmful levels of one or more hazardous materials, such as hazardous gases, hazardous chemical compounds, or hazardous radiation while working in the hazardous work environment. The users 120A-N may suffer from sickness or death if they are exposed to harmful levels of the hazardous materials, such as hazardous gases, chemicals and/or nuclear particles. Alternatively or in addition, the users 120A-N may be deprived of oxygen, such as in a mine, and may suffer from sickness or death from lack of oxygen. The work environment, or work area, may include multiple structures, such as buildings, and each building may include multiple levels or floors. The work environment may further include one or more outdoor areas, and/or subterranean areas, such as a basement, tunnel or cave. The users 120A-N may be located in any of the structures or levels within the work environment.

The users 120A-N may each wear a gas detection and locating device, such as a badge or tag, which may include a sensor for monitoring the exposure of the users 120A-N to the hazardous materials, such as hazardous gases or chemical compounds. The badge may include a hazardous gas sensor, a locating device, and an interface, such as a network interface. The interface may transmit data describing the amount of hazardous gas a user A 120A has been exposed to, and the location of the user A 120A, to a central server. The hazardous gas exposure and location data of the user A 120A may be transmitted to the central server on a periodic basis, such as every minute. The period of time between transmissions of each user 120A-N may be manually configurable and/or may be automatically configurable by the central server. For example, if the central server detects that a user A 120A has entered an area with a high concentration of hazardous gases, the central server may automatically instruct the badge to transmit the gas exposure information of the user A 120A more frequently. Alternatively or in addition, if the hazardous gas exposure of the user A 120A is approaching dangerous levels, the central server may automatically instruct the badge to transmit the gas exposure data more frequently. For example, there may be one or more gas exposure thresholds which, when met by a user A 120A, may cause the badge of the user A 120A to increase the frequency of the transmissions of gas exposure information.

Alternatively or in addition, users 120A-N in a nuclear power plant work environment may wear a radiation detector and locating device. The radiation detector and locating device may include a Geiger counter for determining the exposure of the users 120A-N to radiation. Alternatively or in addition, users 120A-N working in a chemical plant may wear chemical detectors and locating devices which may detect whether the users 120A-N are being exposed to harmful levels of chemical compounds. Alternatively or in addition, users 120A-N working in a mine may wear gas detectors and locating devices which detect whether the users 120A-N are being exposed to enough, or too much, oxygen. In general, the sensor, or detector, worn by the users 120A-N may be determined based on the potential hazards of the work area. The badge should be worn within a breathing zone of the user A 120A, such as within ten inches of the nose and/or mouth of the user A 120A.

Alternatively or in addition, the badge may function as an identification device for the user A 120A. For example, the badge may include a radio frequency identification tag, which may communicate with one or more radio frequency readers. The readers may be in communication with one or more access points, such as doorways. Each reader may either allow or deny the user A 120A to pass through the access point, based on the permissions associated with the radio frequency identification tag of the user A 120A. The radio frequency identification readers may be used as supplemental location devices. That is, the readers may be in communication with the service provider server 240, such as via the networks 230, 235, and may communicate the location and identification of the user A 120A to the service provider sever 240 when the radio frequency identification tag of the user A 120A passes by the reader. Thus, the current location of the user A 120A may be supplemented or verified when the user A 120A passes by one of the radio frequency identification readers.

The badge may further include a location processor, such as a positioning system processor, for determining information describing the location of a user A 120A and communicating the location information to the central server. The positioning processor may determine the location of the user A 120A based on data received from a satellite, such as a global positioning system (GPS). Exemplary badges including location processors are discussed in more detail in FIGS. 5A-B below. Alternatively or in addition, if the user A 120A is located indoors, and the badge is not able to receive data from a satellite, the location of the user A 120A may be identified by the network infrastructure used in the work environment. The components of the network infrastructure are discussed in more detail in FIG. 2 below. The system 100 may be capable of seamlessly switching between identifying the location of the user A 120A through the GPS data or through the network infrastructure, thereby allowing the system 100 to track the location of the user A 120A as they move from indoors to outdoors and vice-versa. If the user A 120A cannot be located through the GPS data or the network infrastructure, the user A 120A may be shown as "out of range" and may reconnect when the user A 120A is back within range of the system 100.

If a badge determines that a user A 120A has been exposed to harmful levels of the hazardous gas, the badge may initiate a local alarm, such as by vibrating, flashing, or sounding an alarm, such as a beep, and may communicate an alarm to the central server including the current location of the user A 120A and the level of gas exposure of the user A 120A. Alternatively or in addition, the central server may determine that the user A 120A has been exposed to harmful levels of the hazardous gases and may communicate a gas exposure alarm to the badge. Detection of harmful levels of hazardous gas by a badge is discussed in more detail in FIG. 6 below.

The badges may also include a panic button, which may be activated by a user A 120A when the user A 120A believes there may be a problem. When a user A 120A activates the panic button, the badge may communicate an alarm to the central server including the location of the user A 120A and the gas exposure of the user A 120A. The badge may also initiate a local alarm. The activation of a panic button on a badge is discussed in more detail in FIG. 7 below.

The badge may also detect if the user A 120A has not moved for a period of time. If the badge detects that the user A 120A has not moved for a period of time, the badge may initiate a local alarm, such as by vibrating, flashing, or sounding a noise. The user A 120A may cancel the lack of motion alarm by pressing a cancel button on the tag or touching their badge. If the user A 120A does not press the cancel button within a period of time, then the badge may communicate an alarm to the central server. Alternatively or in addition, the central server may monitor the movement of the user A 120A and may send a lack of motion alarm to the badge. An alarm related to a lack of motion of the user A 120A may be referred to as a "man down" alarm, or alert, because the user A 120A is presumed to be motionless.

The service provider 140 may provide an organization with the central server, referred to as the service provider server 240 in FIG. 2 below, which receives the location data items and the gas exposure data items from the badges of the users 120A-N. Alternatively or in addition, the service provider 140 may provide the badges to the users 120A-N. For example, the service provider 140 may be consulting organization which provides the badges, and the central server, to the organization in order to enable the organization to monitor the location and gas exposure of their employees. The service provider 140 may customize the server with vendor software for monitoring the location and gas exposure of the users 120A-N. The user interfaces of exemplary monitoring software applications are shown in FIGS. 11-16 below.

The server may receive data transmissions from the badges which may include a location identifier identifying the location of the users 120A-N and the gas exposure of the users 120A-N. The location of the users 120A-N may be determined by a positioning system on the badge, or may be determined by the network infrastructure. The location of the users 120A-N may also include the elevation of the users 120A-N. The location identifier may include coordinates, such longitude and latitude coordinates. The server may determine when a user A 120A has been exposed to harmful levels of gas and may activate an alarm for the user A 120A. Alternatively or in addition, the server may receive an alarm data item from a badge when the badge detects harmful levels of hazardous gases.

The operator 110 may be a person who operates the server provided by the service provider server 140. Alternatively or in addition, the operator 110 may be a machine or automated process. The operator 110 may monitor the users 120A-N and may be alerted by the server when one of the users 120A-N is exposed to harmful levels of the hazardous gases. The operator may attempt to initiate contact with the user A 120A, such as over a walkie-talkie or over a mobile phone. The operator 110 may also initiate communication with emergency personnel, such as responders, if necessary. Alternatively or in addition, there may be one or more operators spread throughout the workplace who may be in communication with the server, such as via a mobile device or other computing device.

In operation, when the server receives an alarm data item or initiates an alarm, such as for a user A 120A who is exposed to harmful levels of a hazardous gas, the server may perform a series of alarm handling actions based on the received alarm data item. The alarm handling actions may include alerting the operator 110 to the alarm, attempting to open a communication channel to the user A 120A, identifying the location of the user A 120A in the facility, and communicate the alarm and the location of the user A 120A to any other operators in the facility. The server may also determine whether emergency responders, such as medical personnel, are required based on the level of gas exposure of the user A 120A, and may automatically initiate communication with the emergency responders. The reception of alarm data by the server is discussed in more detail in FIG. 9 below.

Alternatively or in addition, the service provider 140 may provide a prepackaged solution for real time locating and gas detection which may further include add-on applications. The add-on applications may include video surveillance, unified communications, asset tracking, mobile worker, fixed gas monitoring, gas cloud simulation, and/or productivity, such as worker scheduling and time card reporting. The solution may include a hardware installation template/approach which may describe a process for optimized infrastructure deployment. The solution may include a solution deployment template, which may describe a process used to quickly and accurately deploy the solution. The solution may include change management, which may describe business process changes required by the personnel in the work area, such as a plant or refinery, in order to properly use the solution. The solution may include a communication template which may describe a process used to ensure comprehensive and optimized testing. The solution may include costing model template which may describe a cost estimating model for deployment based on plant layout. The solution may include an ongoing support accelerator, which may describe the management process required for long term support. The service provider 140 may also provide ongoing validation of the solution, such as a process for ensuring that solution/application is functioning properly over time.

Alternatively or in addition, the service provider 140 may identify a single point of contact which may include negotiated vendor contracts and defined vendor responsibilities. The service provider server 240 may also provide z-axis calibration. For example, the service provider 240 may calibrate on the ground and may calibrate in the air.

Alternatively or in addition, the service provider 140 may provide one or more productivity process improvements. For example, the service provider 140 may provide a change maintenance process for managing volatile organic compound (VOC) emissions using wireless gas sensors. The service provider 140 may also provide a change maintenance process for managing volatile organic compound (VOC) transmissions using wireless gas sensors. The service provider 140 may provide architecture to support enterprise level work efficiencies, as existing solutions may be plant/location specific an unable to scale on their own. The service provider 140 may provide process improvements aimed at workforce/resource sharing. The service provider 140 may provide contractor accountability, such as by linking to PEOPLESOFT time and labor reporting to create automated accountability/dashboards/reconciliation and analysis.

Alternatively or in addition, the gas detection devices worn by the users 120A-N may be used in conjunction with stationary wireless gas sensors in order to build a wireless sensor network. An exemplary wireless sensor network is discussed in more detail in FIG. 4 below. The wireless sensor network may be used to predict the movement of a hazardous gas through a work area. Predicting the movement of the hazardous gas may allow an organization to pro-actively alert the users 120A-N to imminent danger. Using a wireless sensor network to predict the movement of hazardous gas is discussed in more detail in FIG. 10 below.

Alternatively or in addition, the service provider 140 may provide 'best process' modeling. For example, the service provider 140 may model ideal work performances physically and through video-ip camera network on a WiFi infrastructure. The service provider 140 may offer playback of the performances to workforce/contractors for safety improvements and work efficiency/quality.

Figure 2:
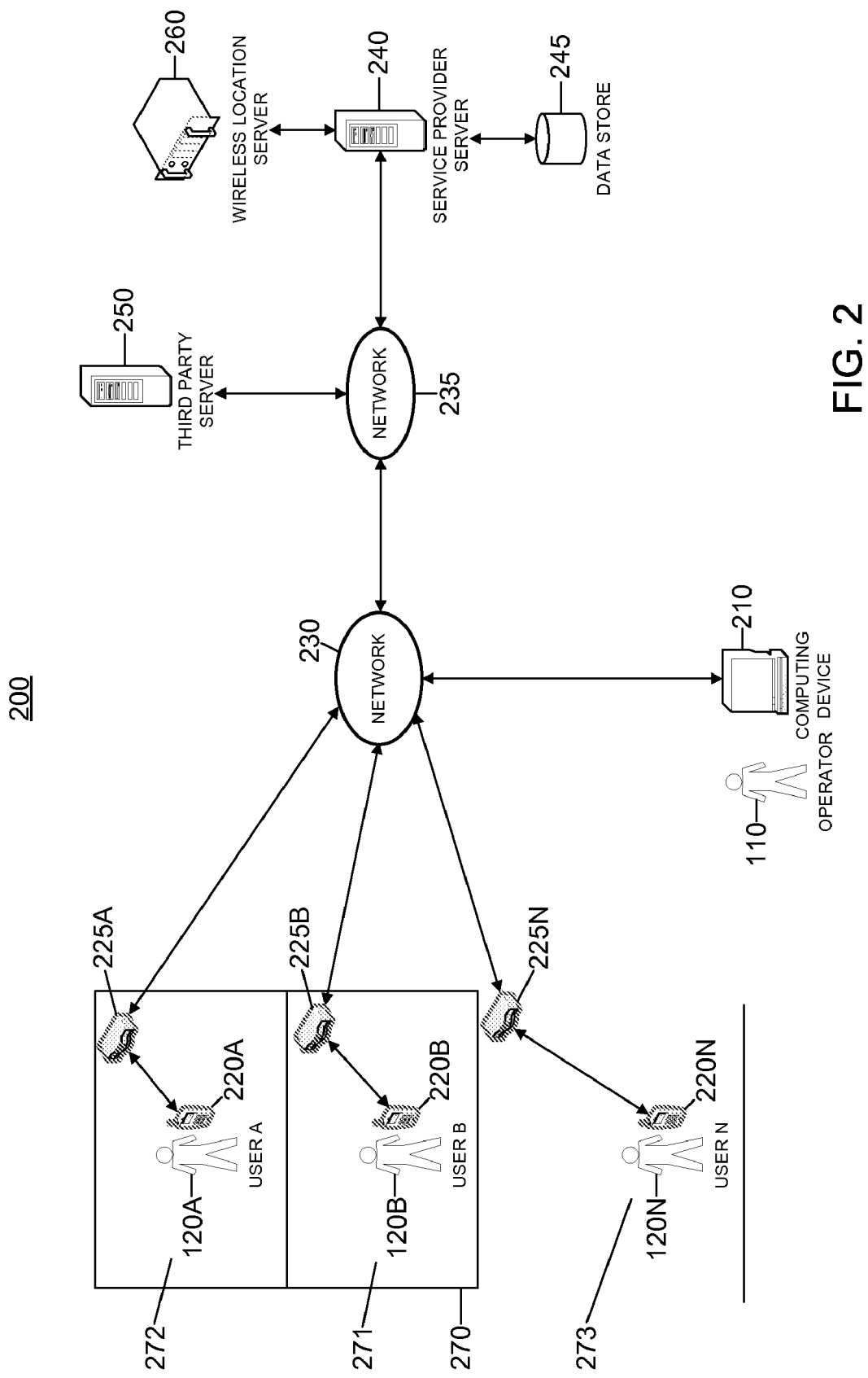
FIG. 2 is a block diagram of a network environment implementing the system of FIG. 1 or other systems for providing real time locating and gas exposure monitoring.

FIG. 2 provides a simplified view of a network environment 200 implementing the system of FIG. 1 or other systems for providing real time locating and gas exposure monitoring. Not all of the depicted components may be required, however, and some implementations may include additional components not shown in the figure. Variations in the arrangement and type of the components may be made without departing from the spirit or scope of the claims as set forth herein. Additional, different or fewer components may be provided.

The network environment 200 may include one or more users 120A-N, gas detection and locating devices ("badges") 220A-N, network components 225A-N, an operator 110, a computing device 210, a service provider server 240, a third party server 250, a data store 245, a wireless location server 260, and networks 230, 235. Some or all of the service provider server 240, the third party server 250, and the wireless location server 260 may be in communication with each other by way of network 235. The users 120A-N may be located across various parts of a facility, or work area, or an organization. The users 120A-B may be located within a structure 270, the user A 120A being on the second floor 272 of the structure 270, and the user B 120B being on the first floor 271 of the structure 270. The user N 120N may be outdoors 273.

The networks 230, 235 may include wide area networks (WAN), such as the Internet, local area networks (LAN), metropolitan area networks, or any other networks that may allow for data communication. The network 230 may include the Internet and may include all or part of network 235; network 235 may include all or part of network 230. The networks 230, 235 may be divided into sub-networks. The sub-networks may allow access to all of the other components connected to the networks 230, 235 in the system 200, or the sub-networks may restrict access between the components connected to the networks 230, 235. The network 235 may be regarded as a public or private network connection and may include, for example, a virtual private network or an encryption or other security mechanism employed over the public Internet, or the like.

The badges 220A-N may be gas detection and locating devices, such as those shown in FIGS. 5A-B below. The badges 220A-N may include a sensor, such as for detecting gas, and a communication interface, such as to communicate over the networks 230, 235. The sensors may be automatically synchronized by the service provider server 240.

Alternatively or in addition, the users 120A-N may receive the badges 220A-N when they are entering a hazardous work area. In this example, the service provider server 240 may scan an identification badge of a user A 120A, such as by bar code or by radio frequency identification, and may then scan a badge 220A. The badge 220A may then be associated with the user A 120A, and the user A 120A may use the badge 220A while in the hazardous work area. When the user A 120A leaves the hazardous work area, they may return the badge 220A and the badge 220A may be unassociated with the user A 120A. For example, the user A 120A may dock the badge 220A into a charger. Upon docking the badge 220A into the charger, the service provider server 240 may remove the association between the badge 220A and the user A 120A. The badge 220A may then be associated with any of the users 120A-N who enters the hazardous work area. Alternatively or in addition, the service provider server 240 may also retrieve any sensor data stored on the badge 220A prior to removing the association from the user A 120A.

The badges 220A-N may communicate over the networks 230, 235 via the network components 225A-N. Each of the network components 225A-N may represent one or more wireless routers, wired routers, switches, controllers, or generally any network components which may be used to provide communications over the networks 230, 235. For example, the network components 225A-N may be CISCO AIRONET Access Points and/or CISCO Wireless LAN Controllers. The network components 225A-N may be capable of identifying the location of the badges 220A-N and communicating the location of the badges to the service provider server 240. In the example where the network components 225A-N are access points, the access points may be strategically placed throughout the facility 270 and/or work area to ensure the entire area of the facility and/or work place is within range of one of the access points. The user N 120N located outdoors 273 may be out of the range of the wireless network, and may communicate with the service provider server 240 via cellular telephone towers. Alternatively, the location of the user N 120N, or the users 120A-B may be determined based on triangulating signals received by cellular telephone towers, third party location services, such as GOOGLE LATITUDE™, or generally any mechanism for determining the location of the user N 120N.

The service provider server 240 may include one or more of the following: an application server, a mobile application server, a data store, a database server, and a middleware server. The service provider server 240 may exist on one machine or may be running in a distributed configuration on one or more machines. The service provider server 240, the computing device 210, the badges 220A-N, and the wireless location server 260 may be one or more computing devices of various kinds, such as the computing device in FIG. 14. Such computing devices may generally include any device that may be configured to perform computation and that may be capable of sending and receiving data communications by way of one or more wired and/or wireless communication interfaces. Such devices may be configured to communicate in accordance with any of a variety of network protocols, including but not limited to protocols within the Transmission Control Protocol/Internet Protocol (TCP/IP) protocol suite. For example, the computing device 210 may employ the Hypertext Transfer Protocol ("HTTP") to request information, such as a web page, from a web server, which may be a process executing on the service provider server 240.

There may be several configurations of database servers, application servers, mobile application servers, and middleware applications included in the service provider server 240. The data store 245 may be part of the service provider server 240 and may be a database server, such as MICROSOFT SQL SERVER®, ORACLE®, IBM DB2®, SQLITE®, or any other database software, relational or otherwise. The application server may be APACHE TOMCAT®, MICROSOFT ITS®, ADOBE COLDFUSION®, or any other application server that supports communication protocols.

The third party server 250 may be a server which provides external data or services to the service provider server 240. For example, the third party server 250 may be part of an emergency response system. The service provider server 240 may request emergency assistance for a user A 120A by communicating with the third party server 250. Alternatively or in addition, the service provider server 240 may provide services or information to the service provider server 240. For example, the third party server 250 may belong to a neighboring business. The service provider server 240 may notify the third party server 250 of gas leaks, such as gas clouds, which may affect the geographical location of the neighboring business based on data received from the badges 220A-N or other gas sensors.

The wireless location server 260 may be a network component capable of identifying the location of the badges 220A-N, and consequently, the location of the users 120A-N. The wireless location server 260 may utilize information received from the network components 225A-N, and/or the badges 220A-N, to determine the location of the users 120A-N. For example, the wireless location server 260 may be a CISCO WIRELESS LOCATION APPLIANCE.

The networks 230, 235 may be configured to couple one computing device, such as the badges 220A-N, to another computing device, such as the service provider server 240, to enable communication of data between the devices. The networks 230, 235 may generally be enabled to employ any form of machine-readable media for communicating information from one device to another. Each of networks 230, 235 may include one or more of a wireless network, a wired network, a local area network (LAN), a wide area network (WAN), a direct connection such as through a Universal Serial Bus (USB) port, and the like, and may include the set of interconnected networks that make up the Internet. If wireless the networks 230, 235 may be cellular telephone networks, 802.11, 802.16, 802.20, or WiMax networks, or generally any wireless network. The networks 230, 235 may include any communication method by which information may travel between computing devices.

The operator 110 may utilize the computing device 110 to monitor the location and the gas exposure of the users 120A-N. The computing device 110 may be configured to run one or more computing applications, such as AEROSCOUT MOBILE VIEW, CISCO WIRELESS CONTROL SYSTEM (WCS) NAVIGATOR or INDUSTRIAL SCIENTIFIC INET CONTROL. The computing applications may assist the operator 110 with monitoring the location and gas exposure of the users 120A-N. The computing applications may utilize Simple Object Access Protocol/Extensible Markup Language (SOAP/XML) application programming interfaces (API) to communicate data with one another. For example, the AEROSCOUT MOBILE VIEW computing application may retrieve data describing the location of the users 120A-N from the CISCO WIRELESS CONTROL SYSTEM using one or more SOAP/XML APIs.

The operator 110 and the computing device 210 may be located within the work area of the organization. Alternatively or in addition, the operator 110 and computing device 210 may be located external to the work area, such as within a remote monitoring facility. The remote monitoring facility may monitor the gas exposure and location of users 120A-N in multiple work areas of multiple organizations.

In operation, a gas sensor in a badge A 220A may detect the level of exposure of a user A 120A to one or more hazardous gases. The badge A 220A may communicate the amount of gas exposure of the user A 120A, and the location of the user A 120A, to the service provider server 240 on a periodic basis. The location of the user A 120A may be determined based on a positioning system, such as a global positioning system (GPS). Alternatively or in addition, if the users 120A-B are located indoors, or the location information can otherwise not be retrieved from a positioning system, the location information may be determined by the network infrastructure. In this example, the wireless location server 260 may determine the location of a user A 120A, such as by triangulating the wireless data signal from the badge A 220A to the network components 225A-N, and may communicate the location of the user A 120A to the service provider server 240. Alternatively, the network components 225A-N may include a radio frequency (RF) reader and may detect the location of the badges 220A-N by triangulating a radio frequency (RF) received from the badges 220A-N.

If the badge A 220A detects that the user A 120A has been exposed to a harmful level of a hazardous gas, the badge A 220A may communicate an alarm to the service provider server 240. The alarm may include the amount of gas the user A 120A has been exposed to and the location of the user A 120A. There may be multiple levels of alarms depending upon the determined danger of the user A 120A. For example, if the user A 120A is not responding to a lack of motion alarm, then an emergency alarm may be issued. However, if the user A 120A is entering a potentially dangerous area, then a warning alarm may be initiated.

The service provider server 240 may receive the alarm data, may transmit an automatic confirmation back to the badge A 120A confirming receipt of the alarm, and may perform one or more alarm response actions based on the alarm data. For example, the service provider server 240 may attempt to initiate communication with the user A 120A, may communicate the alarm to an operator 110 in close proximity of the user A 120A, or, depending on the level of gas exposure, may contact emergency response personnel. The alarm response actions of the service provider server 240 are discussed in more detail in FIG. 9 below.

Alternatively or in addition, the service provider server 240 may monitor the gas exposure information received from the gas detection and locating devices 225A-N and other gas detection devices. The service provider server 240 may analyze the received data to determine areas where the gas level may be dangerously high. If the service provider server 240 detects a user A 120A entering one of the dangerous areas, the service provider server 240 may automatically transmit an alarm to the gas detection and locating device of the user A 120A.

Alternatively or in addition, a plant performance solution, such as ACCENTURE PLANT PERFORMANCE SOLUTION, may be used as an overarching graphical user interface which may be used by the management of the organization. The plant performance solution may be running on the service provider server 240 and/or the computing device 210. The plant performance solution may provide overall plant performance management, such as a heat map display of the alarms. Alternatively or in addition, the service provider server 240 may provide a new graphical user interface depending upon a gap assessment.

Alternatively or in addition, the service provider server 240 may perform one or more analytics on the data collected from the gas detection and locating devices 220A-N and other sensors in the work area. For example, the service provider server 240 may predict high risk work events by integrating the received data with real-time historical/unit level data. Based on the analyzed data, the service provider server 240 may provide proactive alerts to the users 120A-N, managers and/or operators. The service provider server 240 may correlate gas releases to unplanned processes for historical analysis, may plan for future events and may continuously improve the system 100. Generally, the service provider server 240 may maintain historical data gathered from the gas detection and locating devices 220A-N and other sensors to identify trends, such as exposure levels per area, exposure levels per user, or generally any trends.

Alternatively or in addition, the network environment 200 may be tested on a periodic basis, such as each month, to ensure the entire system 100 is operating properly. The network environment 200 may further include additional sensors, such as wireless magnetic temperature sensors, which are in communication with the service provider server 240, such as via the networks 230, 235. Alternatively or in addition, the data received from the gas detection and locating devices 225A-N and/or other sensors, referred to as telemetry data, may be integrated into MSE. Alternatively or in addition, the system 100 and/or one or more components of the network environment 200 may be integrated into DCS.

Alternatively or in addition, there may be multiple operators 110 operating multiple computing devices 210. In this example the service provider server 240 may determine the proper operator 110 for receiving each alarm, such as based on geographic location, language spoken, or other factors.

Alternatively or in addition, the network environment 200 may further include supplemental tags for assistance with determined dead spots. A dead spot may be a location where there is no gas detection or no wireless infrastructure. Alternatively or in addition, the service provider server 240 may include the Experion DCS which may be used for alarming of either gas sensor based alarms of alarms initiate by the activation of the panic button.

Alternatively or in addition, each alarm may indicate the reason for the alarm on both the gas detection and locating devices 220A-N and the computing device 210 of the operator 110. The alarm on the gas detection and locating devices may include an audible tone which may differ for each type of alarm.

Figure 3:
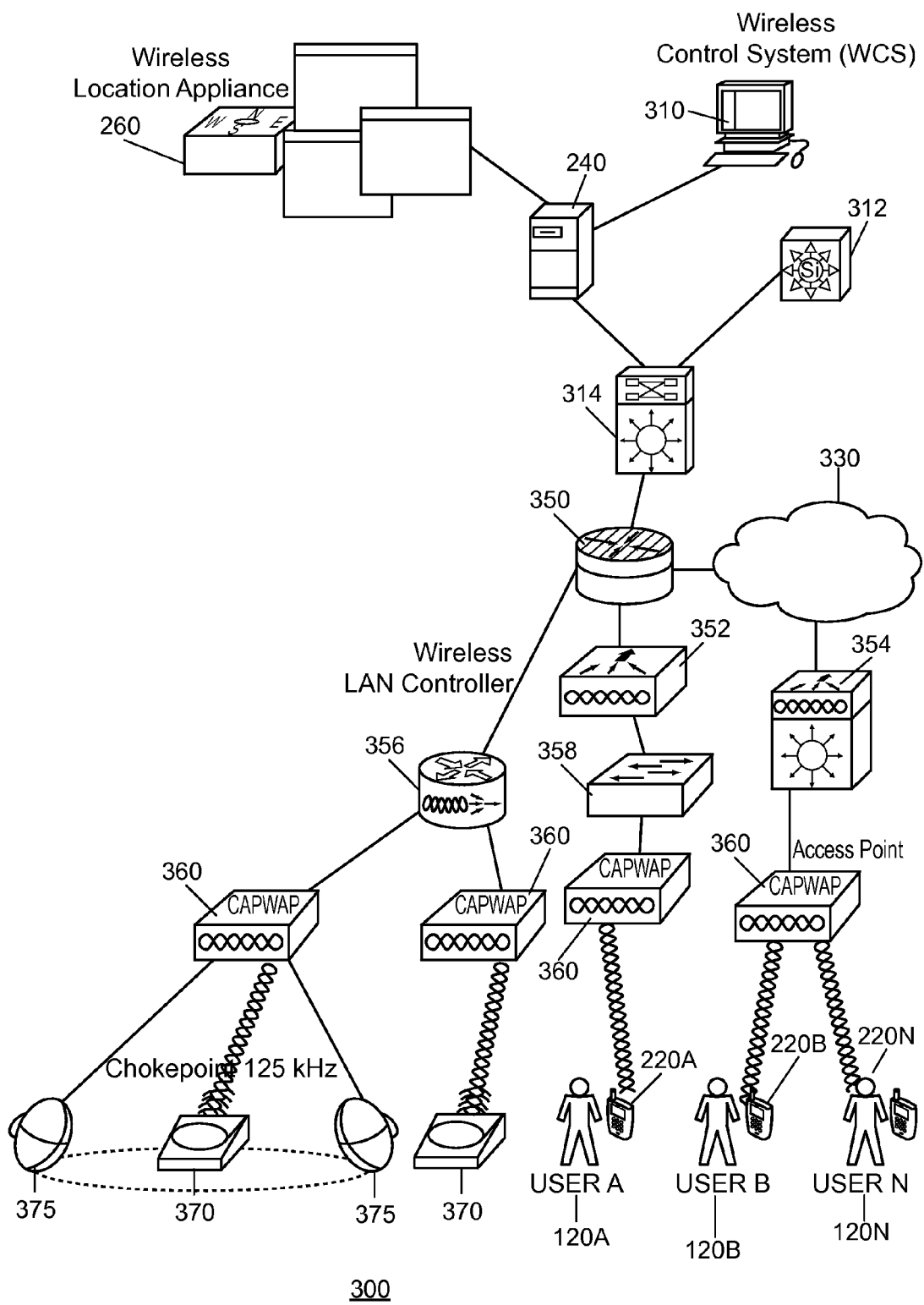
FIG. 3 is a block diagram of an exemplary network architecture implementing the system of FIG. 1 or other systems for providing real time locating and gas exposure monitoring.

FIG. 3 is a block diagram of an exemplary network architecture 300 implementing the system of FIG. 1 or other systems for providing real time locating and gas exposure monitoring. Not all of the depicted components may be required, however, and some implementations may include additional components not shown in the figure. Variations in the arrangement and type of the components may be made without departing from the spirit or scope of the claims as set forth herein. Additional, different or fewer components may be provided.

The network architecture 300 may include a wireless location server 260, a wireless control system 310, a service provider server 240, a multilayer switch 312, a route switch processor 314, a network 330, a router 350, a wireless LAN controller 352, a wireless services module 354, a wireless LAN controller module 356, a switch 358, wireless access points 360, Wi-Fi tags 370, stationary wireless sensors 375, or chokepoints, users 120A-N and badges 220A-N. For example, the wireless location server 260 may be a CISCO WIRELESS LOCATION APPLIANCE, the wireless control system 310 may be a CISCO WIRELESS CONTROL SYSTEM, the wireless LAN controller 352 may be a CISCO WIRELESS LAN CONTROLLER, and the wireless access points 360 may be lightweight wireless access points, such as CISCO AIRONET ACCESS POINTS. Alternatively, or in addition, the wireless access points 360 may be CAPWAP wireless access points.

The stationary wireless sensors 375 may include gas sensors, such as hazardous gas sensors, and may be mounted in areas requiring monitoring. The stationary wireless sensors 375 may detect the presence of the Wi-Fi tags 370 and/or the badges 220A-N. Alternatively or in addition, if the stationary wireless sensors 375 include gas sensors, the stationary wireless sensors 375 may detect the presence of hazardous gases. The sensors of the stationary wireless sensors 375, and the sensors of the badges 220A-N, may function as a sensor network, such as the sensor network described in FIG. 4 below. The controllers 352, 356, may be stationary, or may be mobile, such as located inside a vehicle. In the case of a mobile controller 352, 356, the controller 352, 356 is mobile across high latency links.

Figure 4:
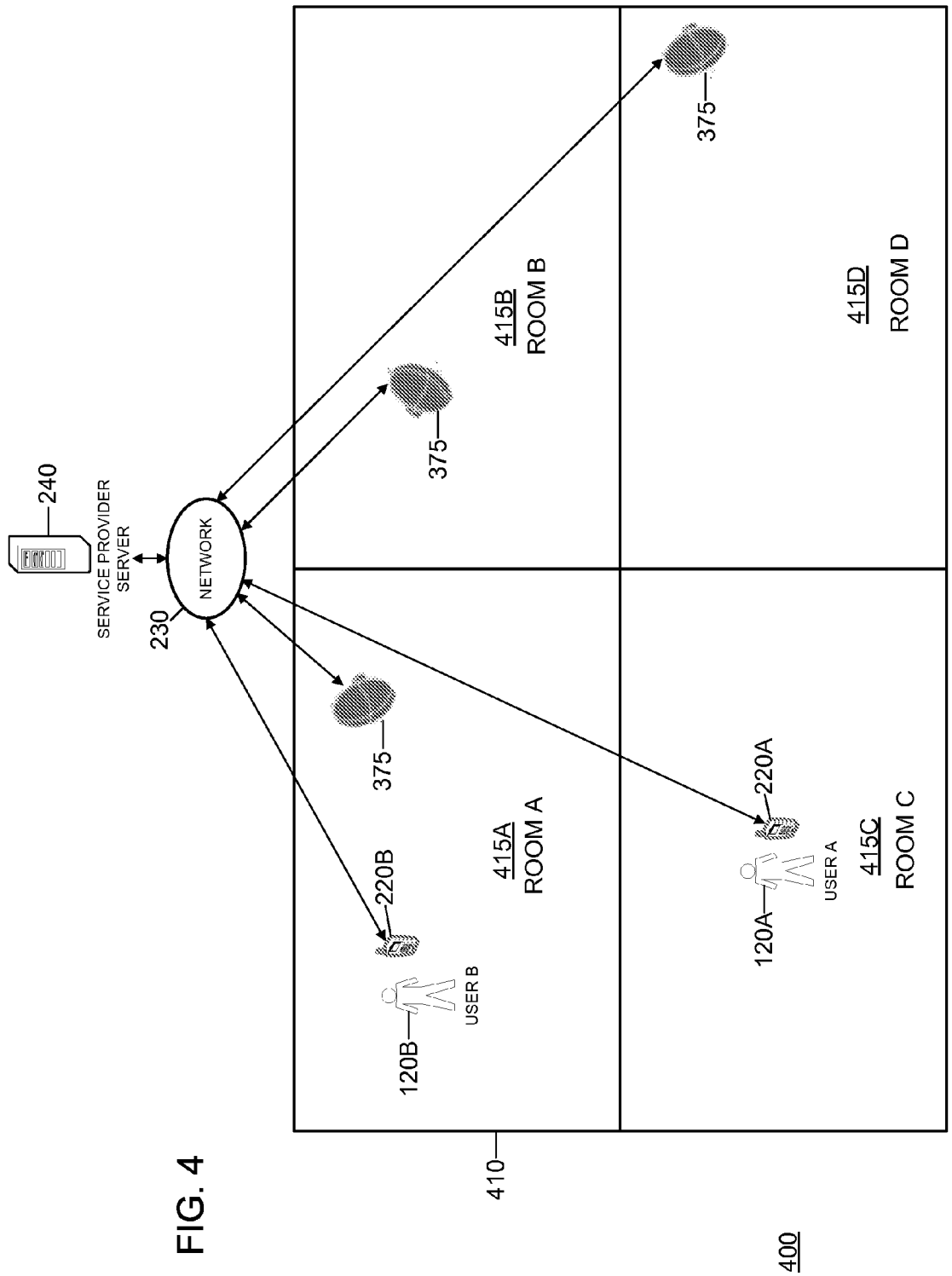
FIG. 4 is a block diagram of a sensor network implementing the system of FIG. 1 or other systems for providing real time locating and gas exposure monitoring.

FIG. 4 is a block diagram of a sensor network 400 implementing the system of FIG. 1 or other systems for providing real time locating and gas exposure monitoring. Not all of the depicted components may be required, however, and some implementations may include additional components not shown in the figure. Variations in the arrangement and type of the components may be made without departing from the spirit or scope of the claims as set forth herein. Additional, different or fewer components may be provided.

The sensor network 400 may include a facility 410, a network 230, and a service provider server 240. The facility may include rooms 415A-D. Room A 415 A may include a user B 120B, a badge B 220B, and a stationary wireless sensor 375. Room B 415B may include a stationary wireless sensor 375. Room C 415C may include a user A 120A, and a badge A 120A. Room D 415D may include a stationary wireless sensor 375. In operation, the badges 220A-B and stationary wireless sensors 375 may detect hazardous gas levels and may communicate the hazardous gas levels to the service provider server 240 through the network 230. The sensor network 400 may also include one or more network components which are not shown in FIG. 4, such as the network components shown in FIG. 3.

The stationary wireless sensors 375 may be mounted in rooms or areas which are not frequently visited by the users 120A-N. For example, the room B 415B and the room D 415D may not be frequently visited by the users 120A-N. Alternatively, sensors 375 may not be placed in rooms or areas where users 120A-N are frequently present. For rooms or areas where users 120A-N are frequently present, the badges 220A-N of the users 120A-N may act as substitutes for the sensors 375. That is, since the users 120A-N wearing badges 220A-N containing sensors are frequently present in these areas, there may not be a need for additional stationary sensors 375. Alternatively or in addition, stationary wireless sensors 375 may be placed in rooms where users 120A-N are frequently present if these areas require a higher level of fidelity in the detection of hazardous gases. In this instance, the service provider server 240 may be able to identify both the specific room where hazardous gas is detected and a particular region of the room where hazardous gas is detected.

The sensor network 400 may also be used to predict the movement of a hazardous gas. For example, the differing levels of a hazardous gas detected by the sensors 375 and the badges 220A-B, along with the rate of change in the levels of the hazardous gas, may be used to predict the movement of the hazardous gas. Predicting the movement of the hazardous gas may allow the service provider server 240 to transmit pro-active alarms to the badges 220A-N of the users 120A-N. That is, the service provider server 240 may transmit alarms to users 120A-N who are not currently in danger, but have a high likelihood of being in danger in a short period of time, such as 5 minutes. Using the sensor network to predict high risk areas is discussed in more detail in FIG. 10 below.

Figure 5A:
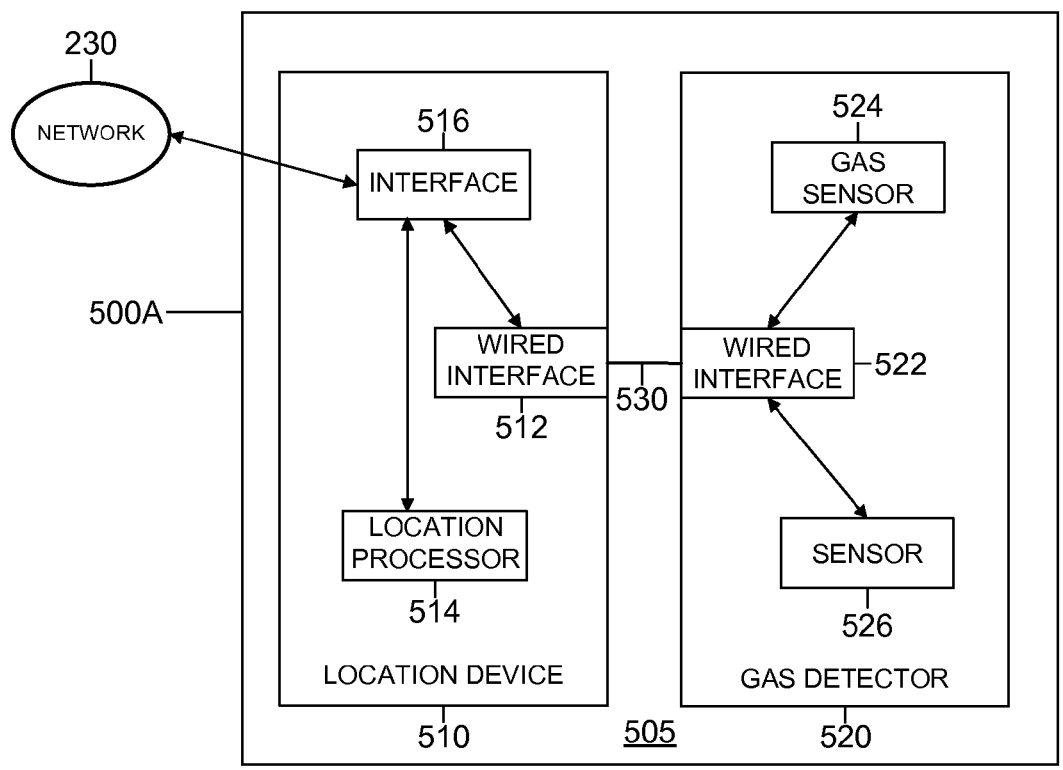
FIG. 5A is a block diagram of an exemplary gas detection and locating device with wired components in the system of FIG. 1 or other systems for providing real time locating and gas exposure monitoring.

FIG. 5A provides an illustration of an exemplary gas detection and locating device 500A with wired components in the system of FIG. 1 or other systems for providing real time locating and gas exposure monitoring. Not all of the depicted components may be required, however, and some implementations may include additional components not shown in the figure. Variations in the arrangement and type of the components may be made without departing from the spirit or scope of the claims as set forth herein. Additional, different or fewer components may be provided.

The gas detection and locating device 500A may be used as one of the badges 220A-N in FIGS. 2-4 above. The gas detection and locating device 500A may include a casing 505, a location device 510, a gas detector 520, and a connector 530. The location device 510 may include a wired interface 512, a location processor 514, and an interface 516, such as a network interface. The gas detector 520 may include a wired interface 522, a gas sensor 524, and a sensor 526. In one example, the location device 510 may be a LENEL badge, or location sensor, or an AEROSCOUT TAG, such as an AEROSCOUT T3 TAG, an AEROSCOUT T4B tag, an AEROSCOUT T5 SENSOR TAG, or an AEROSCOUT T6 GPS TAG, and the gas detector 520 may be an INDUSTRIAL SCIENTIFIC GAS BADGE, such as an INDUSTRIAL SCIENTIFIC GASBADGE PLUS, an INDUSTRIAL SCIENTIFIC MX-4, an INDUSTRIAL SCIENTIFIC MX-6, or an INDUSTRIAL SCIENTIFIC GASBADGE PRO. The casing 505 may be the original housing of the location device 510. In this example, the gas detector 520 would be added to the casing of the location device 510. Alternatively, the casing 505 may be the original housing of the gas detector 520. In this example, the location device 510 would be added to the casing of the gas detector 520.

The location device 510 and the gas detector 520 may be in communication via the connector 530. For example, the wired interface 512 of the location device may be connected to the connector 530, and the connector 530 may be connected to the wired interface 522 of the gas detector. The connector 530 may be a wired connector, such as an RS-232 serial connection cable, a wire, or generally any connector capable of coupling the location device 510 to the gas detector 520. The gas detector 520 may communicate information determined by the gas sensor 524 and/or the sensor 526, such as the amount of gas the user A 120A has been exposed to, to the location device 510.

The location processor 514 of the location device 510 may determine the location of the gas detection and locating device 500A, such as through a positioning system. For example, the location processor 514 may be in communication with one or more GPS satellites, and may receive location information from the GPS satellites. The location processor 514 may communicate the location information to the interface 516. The interface 516 may enable the gas detection and locating device 500A to communicate with the network 230. The interface 516 may be a wireless network connection, a wired network connection, an infrared network connection, or generally any connection capable of providing communication between the gas detection and location device 500A and the network 230. When the location device 510 receives sensor information from the gas detector, the location device 510 may communicate the sensor information, and the current location of the gas detection and locating device 500A to the service provider server 240 via the network 230.

The gas sensor 524 of the gas detector 520 may be a sensor capable of detecting the amount of hazardous gas a user is being exposed to. The gas sensor 524 may be capable of detecting one or more hazardous gases, such as hydrogen sulfide ($H_2S$), nitrogen dioxide ($NO_2$), sulfur dioxide ($SO_2$), carbon dioxide ($CO_2$), carbon monoxide (CO), oxygen ($O_2$), LEL, or generally any gases. In order to ensure the gas sensor 524 is accurately identifying the amount of gas a user A 120A is being exposed to, the gas detection and locating device 500A may be worn close to the mouth and/or nose of the user A 120A, such as within ten inches of the mouth of the user A 120A. The gas sensor 524 may communicate the amount of gas detected to the wired interface 522. The wired interface 522 may communicate the amount of gas detected to the location device 510. Alternatively or in addition, the gas sensor 524, or a coupled processor, may process the amount of gas detected to determine if the amount satisfies an alarm threshold. If the gas sensor 524 determines that the amount satisfies the alarm threshold, the gas sensor 524 may communicate an alarm to the location device 510 via the wired interface 522. Alternatively or in addition, the location processor 514, or a coupled processor, may determine if the amount of gas detected satisfies the alarm threshold.

The sensor 526 may detect other stimuli, such as biometric information or heat exhaustion information. The sensor 526 may communicate the biometric information to the location device 510 via the wired interface 522. Alternatively or in addition, the sensor 526 may detect whether the user A 120A is moving. For example, the sensor 526 may detect that the user A 120A has not moved for an extended period of time. In this instance, the sensor 526 may activate a local alarm on the gas detecting and locating device 500A. The local alarm may cause the gas detection and locating device 500A to vibrate, light up, beep, or otherwise notify the user A 120A of the lack of movement. The user A 120A may respond to the local alarm by pressing a button on the outside of the casing 505. If the user A 120A does not press the button within a period of time, such as ten seconds, the sensor 526 may communicate an alarm to the service provider server 240 via the location device 510.

Alternatively or in addition, the outside of the casing 505 of the gas detection and locating device 500A may include one or more buttons, lights, sensors, and/or displays. For example, the outside of the casing 505 may have a panic button that can be activated by the user A 120A in the case of an emergency. The casing 505 may also have a cancel button, which may allow the user A 120A to cancel an alarm, such as an alarm caused by lack of motion. The casing 505 may also include one or more lights, or displays, which may light up or change colors when the user A 120A is exposed to different levels of gases. Alternatively or in addition, the outside of the casing 505 may include a display which may display the amount of gas the user A 120A is currently being exposed to and whether the current level of exposure is dangerous to the health of the user A 120A. The display may also display the reason an alarm has been initiated by the gas detection and locating device 500A.

Alternatively or in addition, the gas detection and locating device 500A may be intrinsically safe, such as Class I, Division 2, simple and easy to use, reasonably sized, such as no longer than a mobile phone, and able to attach to a front pocket or helmet, such as generally within ten inches of a breathing zone of a user A 120A.

Figure 5B:
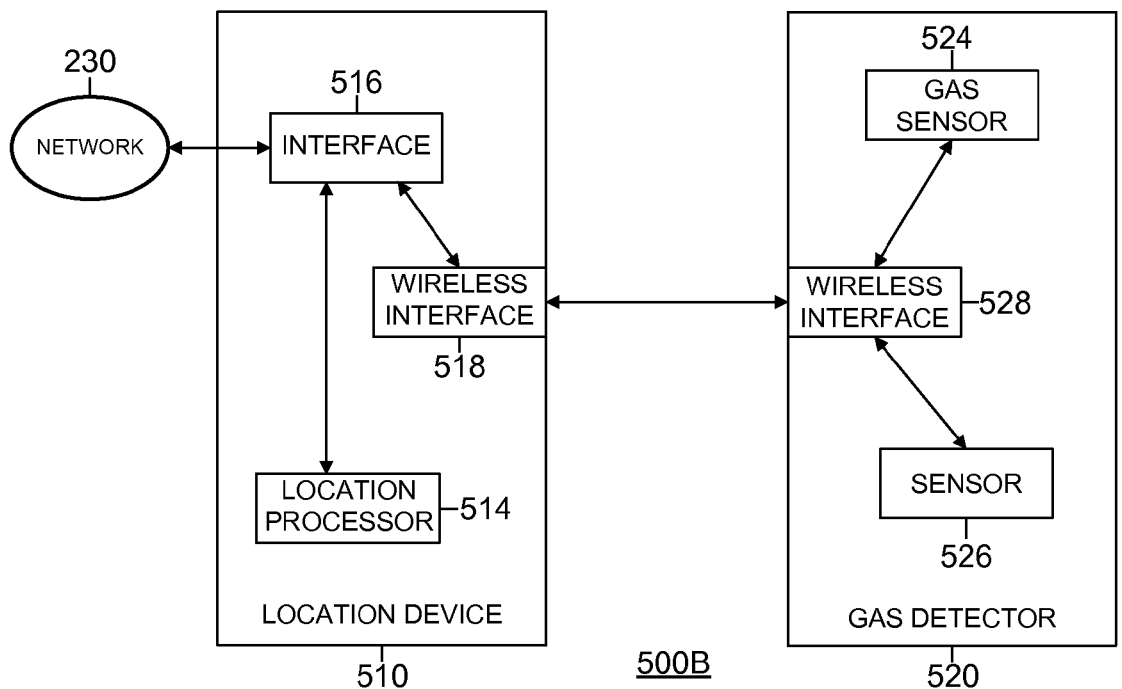
FIG. 5B is a block diagram of an exemplary gas detection device with wireless components in the system of FIG. 1 or other systems for providing real time locating and gas exposure monitoring.

FIG. 5B provides an illustration of an exemplary gas detection and locating device 500B in the system of FIG. 1 or other systems for providing real time locating and gas exposure monitoring. Not all of the depicted components may be required, however, and some implementations may include additional components not shown in the figure. Variations in the arrangement and type of the components may be made without departing from the spirit or scope of the claims as set forth herein. Additional, different or fewer components may be provided.

The gas detection and locating device 500B may be used as one of the badges 220A-N in FIG. 2 above. The gas detection and locating device 500B may include a location device 510 and a gas detector 520. The location device 510 may include a wireless interface 518, a location processor 514, and an interface 516. The gas detector 520 may include a wireless interface 528, a gas sensor 524, and a sensor 526. In one example, the location device 510 may be an AEROSCOUT TAG, such as an AEROSCOUT T3 TAG, an AEROSCOUT T5 SENSOR TAG, or an AEROSCOUT T6 GPS TAG, and the gas detector 520 may be a INDUSTRIAL SCIENTIFIC GAS BADGE, such as an INDUSTRIAL SCIENTIFIC GASBADGE PLUS, an INDUSTRIAL SCIENTIFIC MX-4, an INDUSTRIAL SCIENTIFIC MX-6, or an INDUSTRIAL SCIENTIFIC GASBADGE PRO.

The location device 510 and the gas detector 520 may be in communication via the wireless interfaces 518, 528. The wireless interfaces 518, 528 may communicate via one or more wireless communication protocols, such as Bluetooth, infrared, Wi-Fi, wireless universal serial bus (USB), radio frequency, or generally any wireless communication protocol. The gas detector 520 may communicate information determined by the gas sensor 524 and/or the sensor 526, such as the amount of gas the user A 120A has been exposed to, to the location device 510 via the wireless interfaces 518, 528. The wireless interfaces 518, 528, may allow for the location device 510 to be located remotely from the gas detector 520, on the user A 120A. For example, the gas detector may be part of an identification badge which may be within a certain distance of the mouth and/or nose of the user A 120A, such as ten inches. However, the location device 510, may be in the pocket of the user A 120A, or may be clipped to the belt of the user A 120A, thus reducing the size and weight of the identification badge.

The location processor 514 of the location device 510 may determine the location of the gas detection and locating device 500A, such as through a positioning system. For example, the location processor 514 may be in communication with one or more GPS satellites, and may receive location information from the GPS satellites. The location processor 514 may communicate the location information to the interface 516. The interface 516 may enable the gas detection and locating device 500A to communicate with the network 230. The interface 516 may be a wireless network connection, a wired network connection, an infrared network connection, or generally any connection capable of providing communication between the gas detection and location device 500A and the network 230. When the location device 510 receives sensor information from the gas detector, the location device 510 may communicate the sensor information, and the current location of the gas detection and locating device 500A to the service provider server 240 via the network 230.

The gas sensor 524 of the gas detector 520 may be a sensor capable of detecting the amount of hazardous gas a user is being exposed to. The gas sensor 524 may be capable of detecting one or more hazardous gases, such as hydrogen sulfide, nitrogen dioxide, sulfur dioxide, carbon dioxide, carbon monoxide, or generally any gases. In order to ensure the gas sensor 524 is accurately identifying the amount of gas a user A 120A is being exposed to, the gas detection and locating device 500A may be worn close to the mouth and/or nose of the user A 120A, such as within ten inches of the mouth of the user A 120A. The gas sensor 524 may communicate the amount of gas detected to the wired interface 522. The wired interface 522 may communicate the amount of gas detected to the location device 510. Alternatively or in addition, the gas sensor 524, or a coupled processor, may process the amount of gas detected to determine if the amount satisfies an alarm threshold. If the gas sensor 524 determines that the amount satisfies the alarm threshold, the gas sensor 524 may communicate an alarm to the location device 510 via the wired interface 522. Alternatively or in addition, the location processor 514, or a coupled processor, may determine if the amount of gas detected satisfies the alarm threshold.

The sensor 526 may detect other stimuli, such as biometric information. The sensor 526 may communicate the biometric information to the location device 510 via the wired interface 522. Alternatively or in addition, the sensor 526 may detect whether the user A 120A is moving. For example, the sensor 526 may detect that the user A 120A has not moved for an extended period of time. In this instance, the sensor 526 may activate a local alarm on the gas detecting and locating device 500A. The local alarm may cause the gas detection and locating device 500A to vibrate, light up, beep, or otherwise notify the user A 120A of the lack of movement. The user A 120A may respond to the local alarm by pressing a button on the outside of the location device 510 and/or the gas detector 520. If the user A 120A does not press the button within a period of time, such as ten seconds, the sensor 526 may communicate an alarm to the service provider server 240 via the location device 510.

Alternatively or in addition, the outside casing of the location device 510 and/or the gas detector 520 may include one or more buttons, lights, sensors, and/or displays. For example, the outside casing of the location device 510 and/or the gas detector 520 may include a panic button that may be activated by the user A 120A in the case of an emergency. The outside casing of the location device 510 and/or the gas detector 520 may also include a cancel button, which may allow the user A 120A to cancel an alarm, such as an alarm caused by lack of motion. The outside of the location device 510 and/or the gas detector 520 may further include one or more lights, or displays, such as a liquid crystal display (LCD) which may light up or change colors when the user A 120A is exposed to different levels of gases. Alternatively or in addition, the outside casing of the location device 510 and/or the gas detector 520 may include a display which may display the amount of gas the user A 120A is currently being exposed to and whether the current level of exposure is dangerous to the health of the user A 120A.

Alternatively or in addition the gas detector 520 may include an interface, such as a network interface, for communicating gas data to the service provider server 240. In this example, the gas detector 520 and the location device 510 may be associated with a user A 120A. For example, there may be record in the data store 245 which associates an identifier of the gas detector 520 and an identifier of the location device 510 with an identifier of the user A 120A. The gas detector 520 may communicate gas data and an identifier of the gas detector 520 to the service provider server 240. The service provider server 240 may use the identifier of the gas detector 520 to retrieve from the data store 245 an identifier of the user A 120A associated with the gas detector 520, and the location device 510 associated with the user A 120A. The service provider server 240 may then request location data from the identified location device 510. Thus, the service provider server 240 is able to communicate individually with the gas detector 520 and the location device 510.

Figure 6:
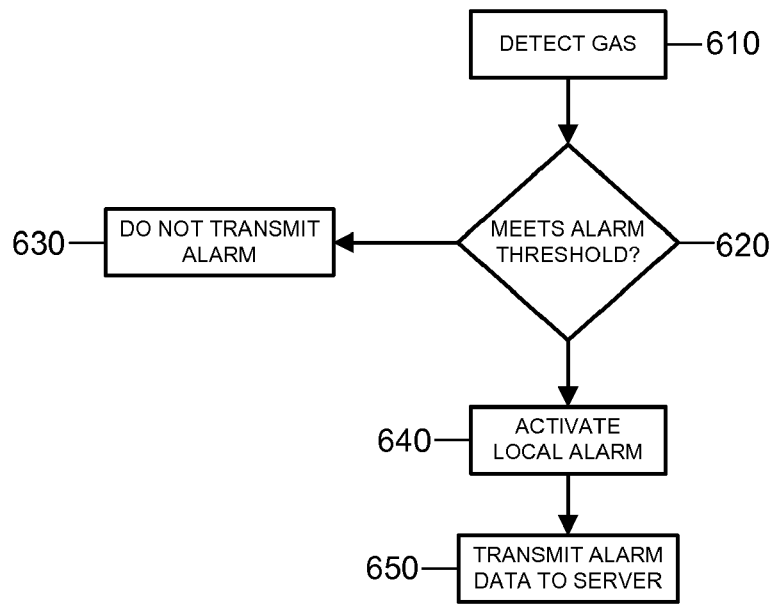
FIG. 6 is a flowchart illustrating the detection of gas by a gas detection and locating device in the system of FIG. 1, or other systems for providing real time locating and gas exposure monitoring.

FIG. 6 is a flowchart illustrating the detection of gas by a gas detection and locating device in the system of FIG. 1, or other systems for providing real time locating and gas exposure monitoring. The steps of FIG. 6 are described as being performed by a gas detection and locating device 500A, 500B. However, the steps may be performed by the processor of the gas detection and locating device 500A, 500B, or by any other hardware component of the gas detection and locating device 500A, 500B. Alternatively the steps may be performed by an external hardware component or software process.

At step 610, the gas detection and locating device 500A may detect a hazardous gas in the vicinity of the user A 120A. For example, the gas sensor 524 of the gas detection and locating device 500A may detect a hazardous gas, such as hydrogen sulfide. At step 620, the gas detection and locating device 500A may determine whether the level of hazardous gas meets an alarm threshold. The alarm threshold may be identified by the operator 110 and may be stored in the data store 245. If, at step 620, the gas detection and locating device 500A determines that the level of gas detected does not meet the alarm threshold, the gas detection and locating device 500A moves to step 630. At step 630, the gas detection and locating device 500A does not transmit an alarm as the level of gas detected does not meet the threshold level.

If, at step 620, the gas detection and locating device 500A determines that the level of gas meets the alarm threshold, the gas detection and locating device 500A moves to step 640. At step 640, the gas detection and location device 500A activates a local alarm. The local alarm may cause the gas detection and locating device 500A to vibrate, flash, play a sound, or otherwise attract the attention of the user A 120A. At step 650, the gas detection and locating device 500A transmits an alarm to the service provider server 240. The alarm data may include the amount of gas the user A 120A has been exposed to, and the location of the user A 120A. For example, the gas sensor 624 may communicate the amount of gas exposure to the location device 610. The location device may retrieve the location of the user A 120A from the location processor 614, if available. The location device 610 may then transmit the amount of gas exposure and the location of the user A 120A to the service provider server 240. Alternatively or in addition, if the location of the user A 120A cannot be determined by the location device 610, the service provider server 240 may retrieve the location of the user A 120A from the wireless location server 260. The service provider server 240 may receive the alarm data item and may perform one or more alarm handling actions based on the alarm data. The actions performed by the service provider server 240 are discussed in more detail in FIG. 9 below.

Alternatively or in addition, the gas detection and locating device 500A may communicate the amount of gas exposure and the location of the user A 120A to the service provider server 240 on a periodic basis, such as every minute. The service provider server 240 may analyze the amount of gas exposure and location of the user A 120A to determine whether the user A 120A has been exposed to harmful levels of gas. If the service provider server 240 determines that the user A 120A has been exposed to harmful levels of gas, the service provider server 240 may communicate an alarm to the gas detection and locating device 500A, and may perform the one or more alarm handling actions. The gas detection and locating device 500A may activate the local alarm. By offloading the processing of the gas exposure data to the service provider server 240, the size and weight of the gas detection and locating device 500A may be reduced.

Figure 7:
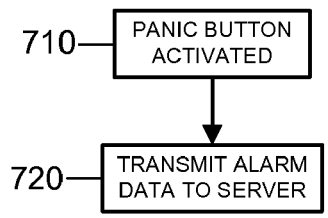
FIG. 7 is a flowchart illustrating a panic button activation by a gas detection and locating device in the system of FIG. 1, or other systems for providing real time locating and gas exposure monitoring.

FIG. 7 is a flowchart illustrating a panic button activation by a gas detection and locating device in the system of FIG. 1, or other systems for providing real time locating and gas exposure monitoring. The steps of FIG. 7 are described as being performed by a gas detection and locating device 500A, 500B. However, the steps may be performed by the processor of the gas detection and locating device 500A, 500B, or by any other hardware component of the gas detection and locating device 500A, 500B. Alternatively the steps may be performed by an external hardware component or software process.

At step 710, the gas detection and locating device 500A may detect that the panic button on the outside of the casing 505 of the gas detection and locating device 500A has been activated, such as when a user A 120A presses the panic button. At step 720, the location device 510 may transmit an alarm to the service provider server 240. The alarm data item may include the current gas exposure of the user A 120A, as detected by the gas sensor 524, and the current location of the user A 120A. The service provider server 240 may receive the alarm data item and may perform one or more alarm response actions based on the received alarm data item. The alarm response actions are discussed in more detail in FIG. 9 below.

Figure 8:
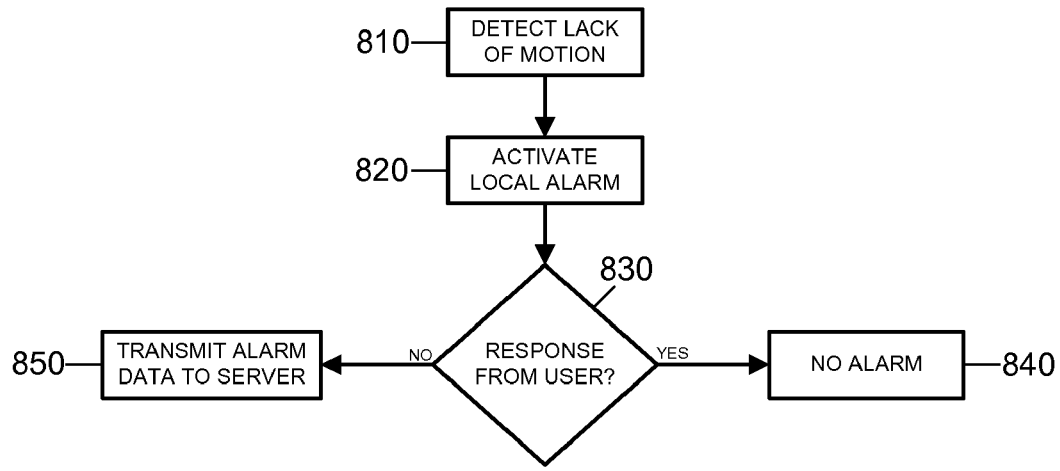
FIG. 8 is a flowchart illustrating a lack of motion detection by a gas detection and locating device in the system of FIG. 1, or other systems for providing real time locating and gas exposure monitoring.

FIG. 8 is a flowchart illustrating a lack of motion detection by a gas detection and locating device in the system of FIG. 1, or other systems for providing real time locating and gas exposure monitoring. The steps of FIG. 8 are described as being performed by a gas detection and locating device 500A, 500B. However, the steps may be performed by the processor of the gas detection and locating device 500A, 500B, or by any other hardware component of the gas detection and locating device 500A, 500B. Alternatively the steps may be performed by an external hardware component or software process.

At step 810, the gas detection and locating device 500A may detect a lack of motion by the user A 120A. For example, the gas detection and locating device 500A may detect that the user A 120A has not moved locations for a period of time. The period of time may be configured by the operator 110, and may be any period of time, such as one minute. The operator 110 may configure different periods of time for each user 120A-N, such as based on the age of the users 120A-N, or other demographic information of the users 120A-N. Alternatively or in addition, the period of time may be based on the current location of a user A 120A. For example, if the user A 120A is in a cafeteria, then the user A 120A may be expected to be stationary for an extended period of time. Thus, the period of time may be longer when the user A 120A is located in a cafeteria. However, when the user A 120A is located within a hallway, the user A 120A may be expected to be continuously moving, and therefore the period of time may be shorter. Alternatively or in addition, the gas detecting and location device 500A may include an accelerometer. The accelerometer may be able to detect motion of the user A 120A. Thus, if the accelerometer does not detect any motion for a period of time, a lack of motion alarm may be initiated.

Alternatively or in addition, the service provider server 240 may monitor the movement of the user A 120A and may detect that the user A 120A has not moved for the period of time. In this instance, the service provider server 240 may communicate a lack of motion alarm to the gas detection and locating device 500A, which may cause the gas detection and locating device 500A to move to step 820.

At step 820, the gas detection and locating device 500A may activate a local alarm. As mentioned above, the local alarm may cause the gas detection and locating device 500A to vibrate, light up, play a sound, or otherwise attract the attention of the user A 120A. At step 830, the gas detection and locating device 500A determines whether the user A 120A responded to the local alarm within a response time. For example, the user A 120A may press a button on the casing 505 of the gas detection and locating device 500A to acknowledge the alarm and verify that there is not a problem. Alternatively or in addition, the user A 120A may press another button on the casing 505 of the gas detection and locating device to indicate that there is a problem. The response time may be configurable and may be determined by the operator 110. The response time may be any period of time, such as five seconds.

If, at step 820, the gas detection and locating device 500A determines that the user A 120A presses the button indicating that there is no problem within the response time, the gas detection and locating device 500A moves to step 840. At step 840, the gas detection and locating device 500A closes the alarm. If the alarm was initiated by the service provider server 240, the gas detection and locating device 500A transmits an indication that the alarm should be closed to the service provider server 240.

If, at step 820, the gas detection and locating device 500A determines that the user A 120A did not press the button within the response time, or the user A 120A pressed the button indicating that there is a problem, the gas detection and locating device 500A moves to step 850. At step 850, the gas detection and locating device transmits an alarm to the service provider server 240. The alarm data may include the amount of gas the user A 120A was exposed to and the current location of the user A 120A. The service provider server 240 may receive the alarm data and may perform one or more alarm response actions based on the alarm data. The alarm response actions performed by the service provider server 240 are discussed in more detail in FIG. 9 below.

Figure 9:
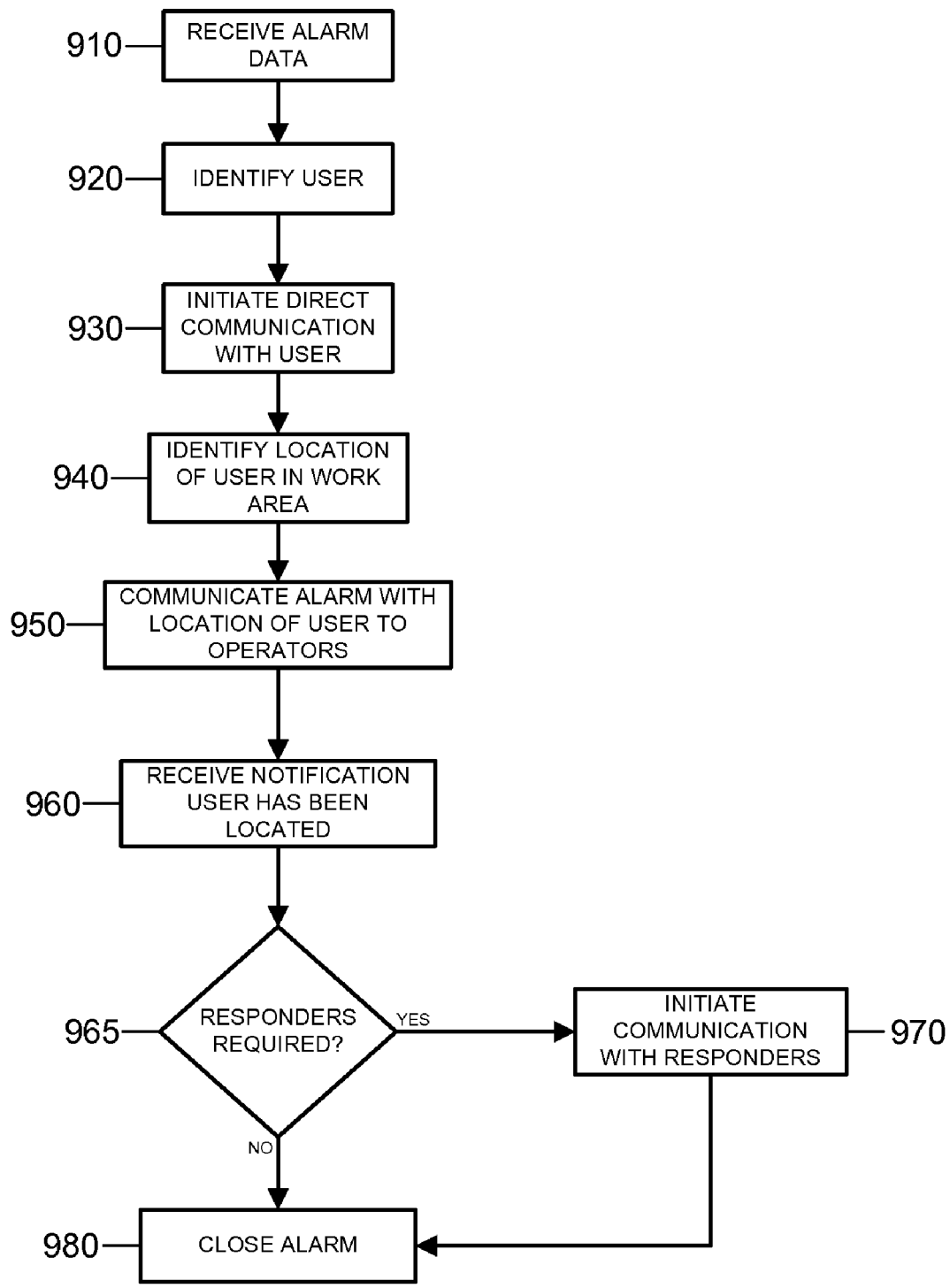
FIG. 9 is a flowchart illustrating an alarm received from a gas detection and locating device in the system of FIG. 1, or other systems for providing real time locating and gas exposure monitoring.

FIG. 9 is a flowchart illustrating an alarm received from a gas detection and locating device in the system of FIG. 1, or other systems for providing real time locating and gas exposure monitoring. The steps of FIG. 9 are described as being performed by the service provider server 240. However, the steps may be performed by the processor of the service provider server 240, or by any other hardware component of the service provider server 240. Alternatively the steps may be performed by an external hardware component or software process.

At step 910, the service provider server 240 may receive alarm data, such as from one of the gas detection and locating devices 220A-N, such as the gas detection and locating device A 220A. The alarm data may have been transmitted to the service provider server 240 in response to the panic button being pressed, the user A 120A being exposed to an unhealthy level of hazardous gas, the user A 120A not responding to a lack of motion alarm within the response period, or generally any other alarm related to the activity of the user A 120A in the work area.

At step 920, the service provider server 240 may identify the individual. For example, the alarm data communicated to the service provider server 240 may include information identifying the user A 120A, or identifying the gas detection and locating device A 220A. If the information identifies the gas detection and locating device A 220A, the service provider server 240 may retrieve data from the data store 245 to determine the user A 120A associated with the gas detection and locating device A 220A.

At step 930, the service provider server 240 may initiate communication with the user A 120A in the field. For example, the service provider server 240 may automatically attempt to connect the operator 110 to the walkie-talkie of the user A 120A, or the mobile phone of the user A 120A. The service provider server 240 may retrieve the walkie-talkie and/or mobile phone information of the user A 120A from the data store 245. The operator may inform the user A 120A that they have been exposed to harmful amounts of hazardous gas and should evacuate the contaminated area immediately. Alternatively or in addition, the service provider server 240 may utilize an interactive voice response system (IVR). The IVR may automatically connect to the walkie-talkie or mobile device of the user A 120A and may play a message to the user A 120A instructing the user A 120A to evacuate the area immediately.

The service provider server 240 may identify the contaminated area based on the amount of gas the other users 120B-N have been exposed to and the location of the other users 120B-N within the work area. Alternatively or in addition, the service provider server 240 may receive gas level information from one or more stationary gas sensors located throughout the work area. If the service provider server 240 cannot isolate a contaminated area, the service provider server 240 may assume that the entire indoor work area is contaminated.

At step 940, the service provider server 240 may identify the location of the user A 120A in the work area. The location of the user A 120A in the work area may be determined based on the location information received from the gas detection and locating device 500A and/or the network infrastructure, such as the wireless location server 260. At step 950, the service provider server 240 may communicate an alarm, with the location of the user A 120A within the work area, to one or more operators located within the vicinity of the user A 120A. The operators may use mobile devices, such as an APPLE IPHONE, to view the alarm data and view the location of the user A 120A relative to each operator. For example, the mobile device may include a map of the work area, which may display the current location of the operator and the location of the user A 120A. The operators may attempt to reach the user A 120A and evacuate the user A 120A from the area contaminated with the hazardous gas.

Alternatively or in addition, the service provider server 240 may communicate the location of other users 120B-N who also may need to be evacuated from the contaminated area. Although the amount of gas exposure of the users 120A-N may be below the alarm threshold, the service provider server 240 may be able to predict an expected amount of gas exposure of the users 120B-N over a period of time based on the gas exposure of the user A 120A. If the service provider server 240 predicts an amount of gas exposure which meets the alarm threshold for the users 120B-N, the users 120B-N may also be evacuated from the contaminated area.

At step 960, the service provider server 240 may receive notification that the user A 120A has been located by one of the operators. For example, an operator may locate the user A 120A and may activate a button on their mobile device to indicate that the user A 120A has been located. Alternatively or in addition, an operator may initiate a communication with the operator 110 and may inform the operator 110 that the user A 120 has been located. The operator 110 may then update the service provider server 240 via the computing device 210.

At step 965, the service provider server 240 may determine whether emergency responders are required. Emergency responders may include medical personnel, hazardous material (HAZMAT) personnel, security personnel, fire department personnel, or generally any emergency responders. In one example, the operator 110, or one of the operators who locates the user A 120A, may communicate an indication to the service provider server 240 that one or more types of emergency personnel are required. Alternatively or in addition, the service provider server 240 may automatically identify one or more emergency responders required using data received from the gas detection and locating devices 220A-N of the users 120A-N, stationary gas detection devices, fire sensors, and/or any additional sensors the service provider server 240 has access to. For example, the service provider server 240 may determine that fire department personnel are required if one or more fire alarms were triggered. Alternatively or in addition, the service provider server 240 may determine that hazardous material personnel are required if the gas contamination meets a threshold If, at step 965, the service provider server 240 determines that one or more emergency personnel are required, the service provider server 240 moves to step 970. At step 970, the service provider server 240 initiates communication with a communication device of the identified one or more emergency personnel, such as via a voice or data communication. If, at step 965, the service provider server 240 determines that no emergency personnel are required, then the service provider server 240 moves to step 980. At step 980, the service provider server 240 closes the alarm. For example, the operators who located the user A 120A may have evacuated the user A 120A from the contaminated area.

Figure 10:
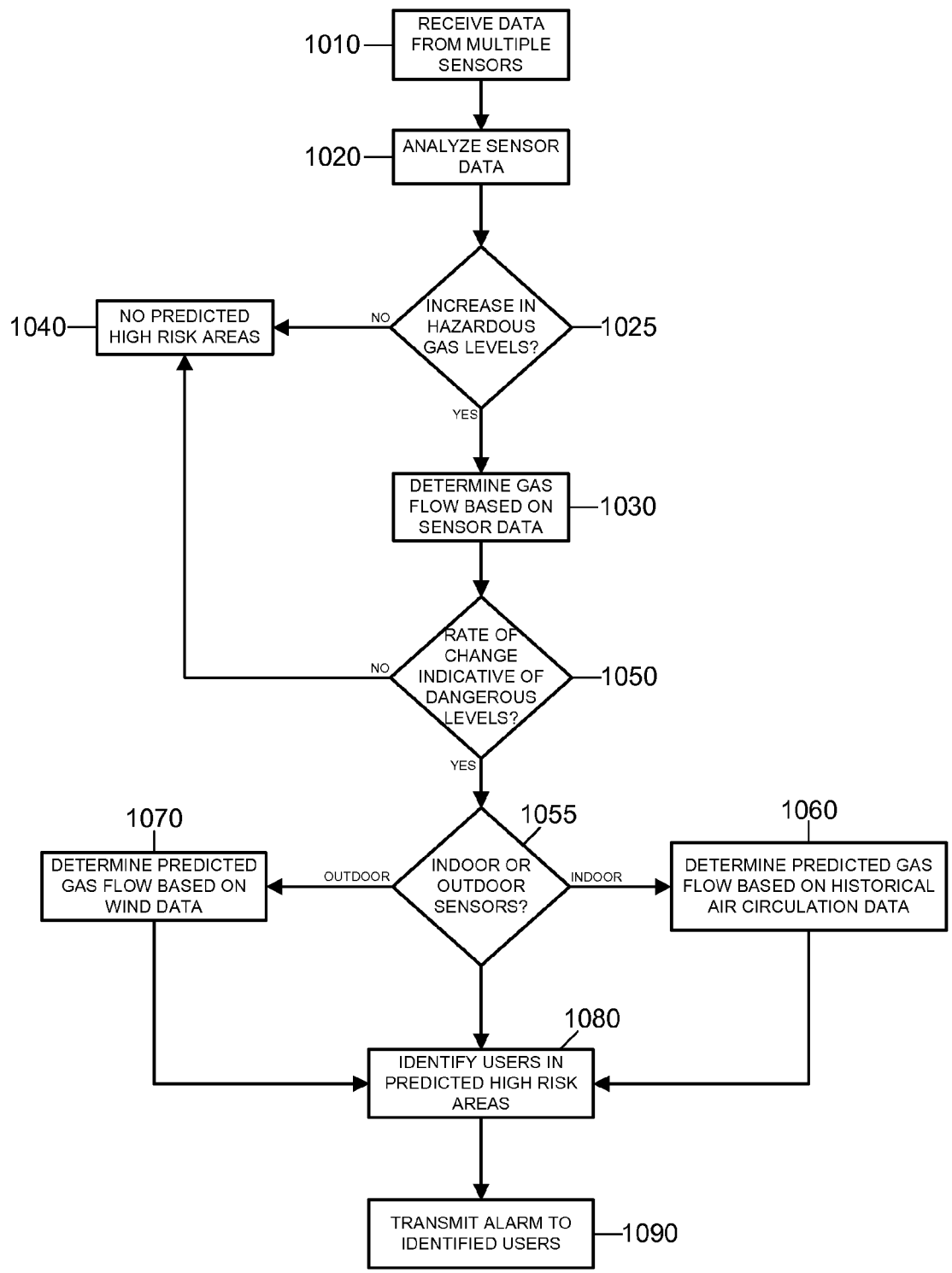
FIG. 10 is a flowchart illustrating high risk area prediction in the system of FIG. 1, or other systems for providing real time locating and gas exposure monitoring.

FIG. 10 is a flowchart illustrating high risk area prediction in the system of FIG. 1, or other systems for providing real time locating and gas exposure monitoring. The steps of FIG. 10 are described as being performed by the service provider server 240. However, the steps may be performed by the processor of the service provider server 240, or by any other hardware component of the service provider server 240. Alternatively the steps may be performed by an external hardware component or software process.

At step 1010, the service provider server 240 may receive sensor data, such as a hazardous gas level, from multiple sensors. The sensors may include sensors within the badges 220A-N, and/or stationary wireless sensors 375. At step 1020, the service provider server 240 may analyze the sensor data. For example, the service provider server 240 may determine whether the level of hazardous gas is increasing or decreasing for each sensor, and may determine the rate of change of the level of hazardous gas for each sensor. At step 1025, the service provider server 240 may determine whether there has been an increase in the level of hazardous gas for one or more sensors. If, at step 1025, the service provider server 240 determines that there has not been an increase in any of the gas levels, the service provider server 240 moves to step 1040. At step 1040, the service provider server 240 determines there are no predicted high risk areas.

If, at step 1025, the service provider server 240 determines that there is an increase in the gas levels detected by one or more of the sensors, the service provider server 240 moves to step 1030. At step 1030, the service provider server 240 determines the rate of change in the detected gas levels, such as based on the last several measurements received from the sensors. For example, if the gas levels are communicated from the sensors to the service provider server 240 every minute, the service provider server 240 may determine the rate of change over the last five minutes. At step 1050, the service provider server 240 determines whether the rate of change of the gas levels indicates that dangerous levels of the hazardous gas may be imminent. For example, the service provider server 240 may identify a dangerous level of the hazardous gas and may determine, based on the rate of change in gas levels, whether the levels of the hazardous gas may reach the dangerous level.

If, at step 1050, the service provider server 240 determines that the rate of change of the gas levels does not indicate that dangerous levels of the gas are imminent, the service provider server 240 moves to step 1040. At step 1040, the service provider server 240 determines there are no predicted high risk areas. If, at step 1050, the service provider server 240 determines the rate of change of the hazardous gas level is indicative of imminent dangerous levels of the hazardous gas, the service provider server 240 moves to step 1055. At step 1055, the service provider server 240 determines whether the sensors in proximity to the imminent dangerous levels of the hazardous gas are located indoors or outdoors.

If, at step 1055, the service provider server 240 determines the sensors are located outdoors, the service provider server 240 moves to step 1070. At step 1070, the service provider server 240 determines a predicted flow of the hazardous gas based on data describing the current direction and rate, or strength, of the wind. For example, if the wind is blowing in a southerly direction, then the gas may be likely to move to the south. Alternatively or in addition, the service provider server 240 may utilize historical sensor readings to determine how quickly the direction and rate of the wind may result in a dissipation of the hazardous gas.

If, at step 1055 the service provider server 240 determines that the sensors are located indoors, the service provider server 240 moves to step 1060. At step 1060, the service provider server 240 determines a predicted flow, or movement, of the hazardous gas based on historical sensor readings which are indicative of the circulation of the air indoors. For example, the historical progression of a gas through the sensor network can be analyzed by reviewing historical sensor measurements. The service provider server 240 may generate a gas flow model based on the historical sensor data and may use the gas flow model to predict the movement of the hazardous gas.

At step 1080, the service provider server 240 may identify the users 120A-N who are located in areas which are predicted to have high levels of the hazardous gas in the near future, such as within the next five minutes, the next ten minutes, or generally any time interval. The users 120A-N may be identified based on the badges 220A-N of the users 120A-N. At step 1090, the service provider server 240 may transmit a pre-emptive, or pro-active, alarm to the badges 220A-N of the users 120A-N who are located in the areas which are predicted to have high levels of hazardous gas in the near future. The users 120A-N may receive the alerts and may evacuate the high risk areas.

Alternatively or in addition, the service provider server 240 may use the data retrieved from the sensors and the gas flow predictive model to determine which vents to open and/or close, such as to contain the hazardous gas. For example, the service provider server 240 may shut one or more vents to isolate the hazardous gas within a confined area, such as an evacuated room. Alternatively, the service provider server 240 may open vents to provide uncontaminated air to an area with high levels of the hazardous gas.

Figure 11:
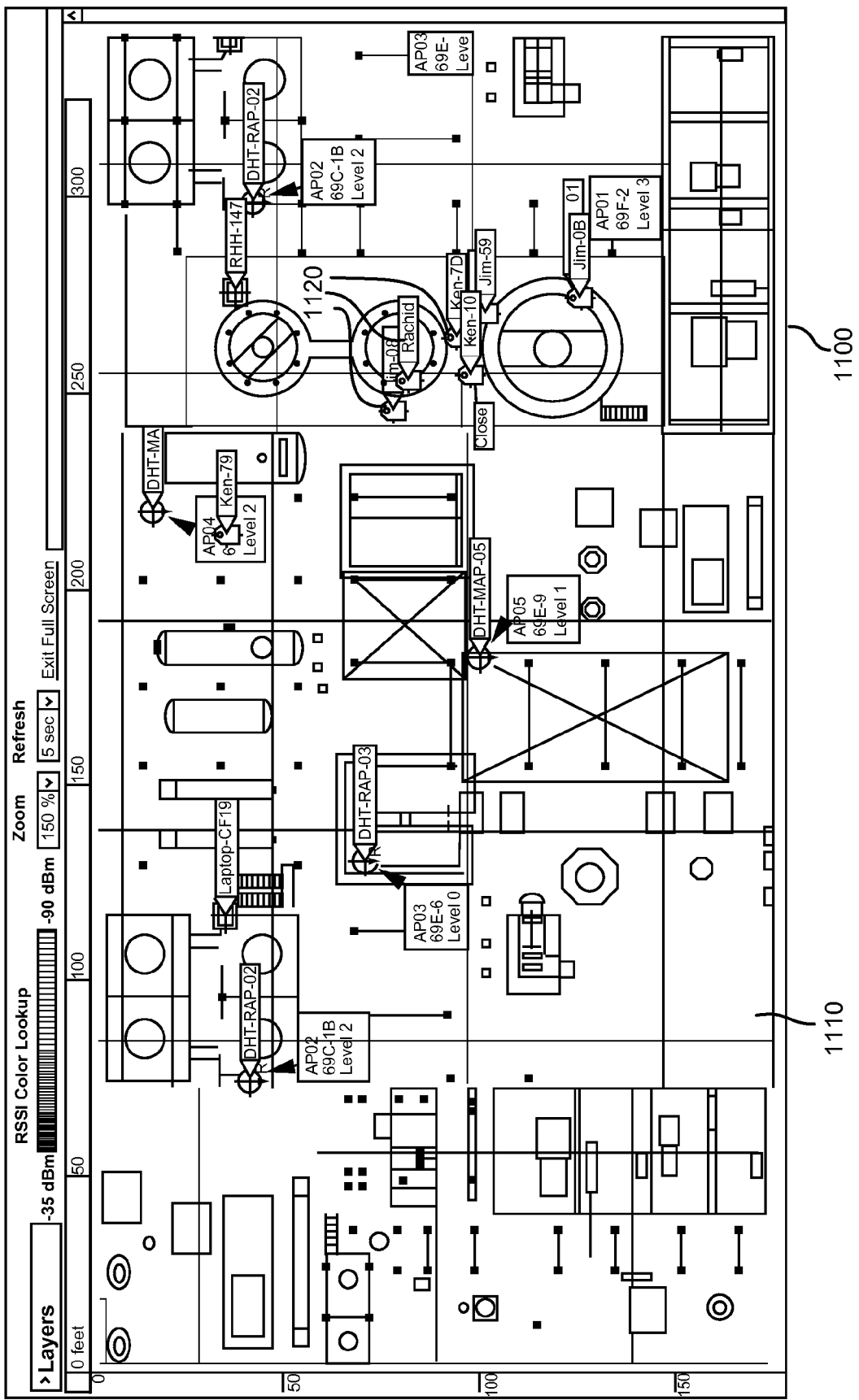
FIG. 11 is a screenshot of a user interface for monitoring the location and gas exposure level of users in the system of FIG. 1, or other systems for providing real time locating and gas exposure monitoring.

FIG. 11 is a screenshot of a user interface 1100 for monitoring the location and gas exposure level of users in the system of FIG. 1, or other systems for providing real time locating and gas exposure monitoring. The user interface 1100 may include a map 1110 and one or more user identifiers 1120. The user identifiers 1120 may indicate the location of the users 120A-N in the workplace. Alternatively or in addition, the user identifiers 1120 may also display the amount of gas each user 120A-N has been exposed to. The user identifiers may change colors based on the amount of gas each user 120A-N has been exposed to. For example, if a user A 120A has been exposed to small amounts of gas, the user identifier 1120 of the user A 120A may be green. Alternatively, if a user B 120B has been exposed to large amounts of gas, the user identifier 1120 of the user B 120B may be red. The user identifier 1120 of a user B 120B who has been exposed to large amounts of gas may also flash or otherwise be displayed visually distinct from the other user identifiers 1120.

In operation, the user interface 1100 may be provided to the operator 110 via the computing device 210. The operator 110 may use the user interface 1100 to monitor the location and amount of gas exposure of the users 120A-N. The operator 110 may use the user interface 1100 to initiate a manual alarm for one or more users 120A-N. The alarm may be transmitted to the gas detection and locating device 220A-N of the users 120A-N by the service provider server 240. For example, if the operator 110 identifies a reason the users 120A-N should be evacuated, such as a tornado or other weather related issue, the operator 110 may initiate a manual alarm. Alternatively or in addition, the service provider server 240 may be in communication with one or more third party servers 250 which provide severe weather alerts. The service provider server 240 may automatically initiate an alarm for all of the users 120A-N if the service provider server 240 receives indication of imminent severe weather, such as a tornado or flood.

Alternatively or in addition, when an alarm is received, the user interface 1100 may be provided to a mobile device of one or more operators located within the vicinity of the user A 120A associated with the alarm. The operators may use the user interface 1100 to locate the user A 120A. Alternatively or in addition, the user interface 1100 may display directions to each operator to locate the user A 120A based on the current location of each operator. Alternatively or in addition, the mobile device of each operator may provide audible directions to each operator.

Alternatively or in addition, if a "man down" alarm is received for a user A 120A, the user interface 1100 may be configured to quickly open and zoom to the location of the user A 120A. Alternatively or in addition, the user interface 1100 may be used to view a simulation of the effect of a gas leak, or gas cloud, on the work area. The user interface 1100 may also include time on tools calculation, which may provide a maintenance productivity calculation.

Figure 12:
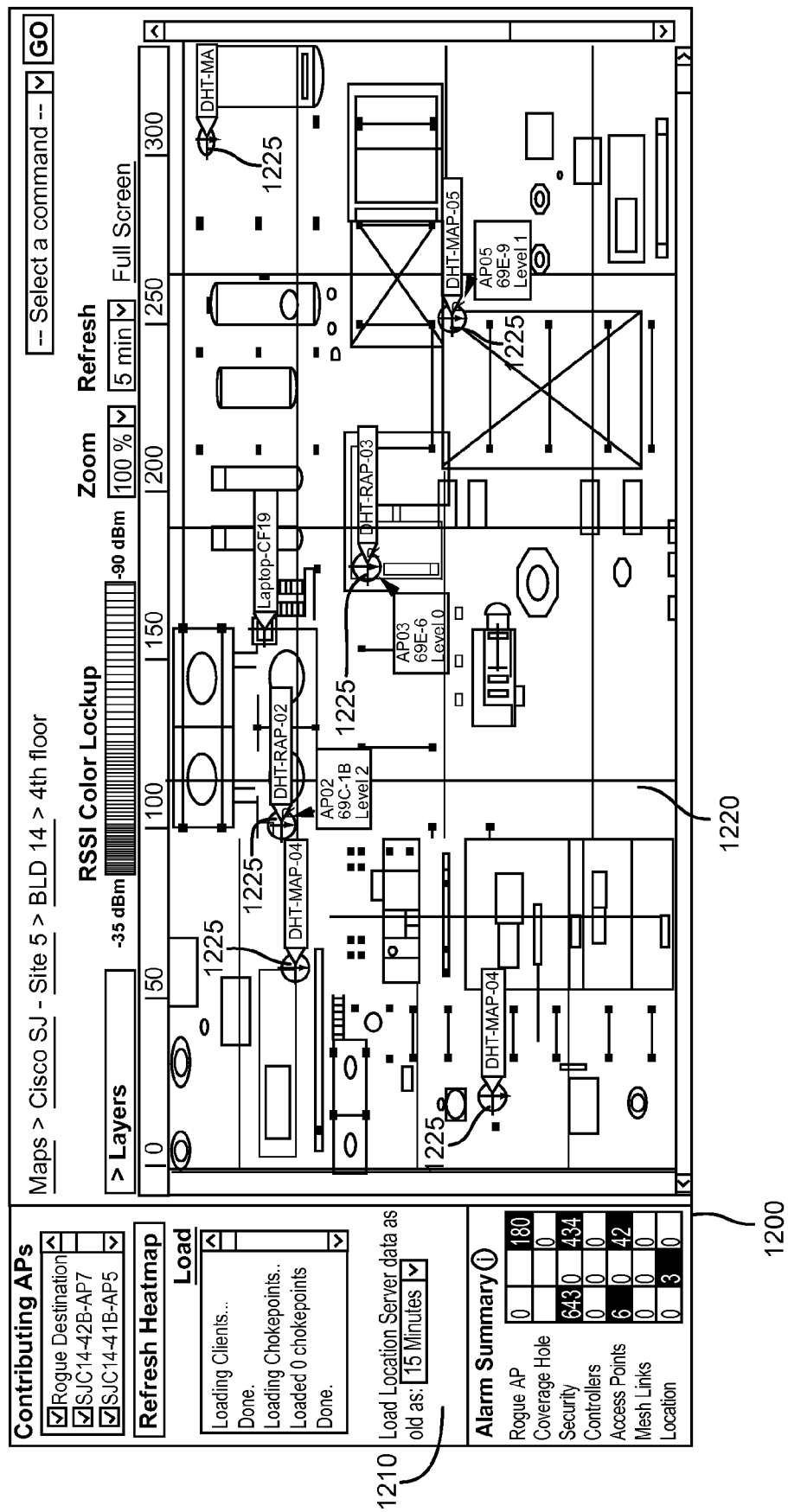
FIG. 12 is a screenshot of a user interface for monitoring gas exposure levels in the system of FIG. 1, or other systems for providing real time locating and gas exposure monitoring.

FIG. 12 is a screenshot of a user interface 1200 for monitoring gas exposure levels in the system of FIG. 1, or other systems for providing real time locating and gas exposure monitoring. The user interface 1200 may include a selection interface 1210 and a gas level display 1220. The gas level display 1220 may include one or more gas sensors 1225. The selection interface 1210 may allow the user A 120A to select one or more options, or filters, which may affect the format or display of the gas levels on the gas level display 1220. The gas level display 1220 may display the location of the gas sensors 1225 and the levels of gas detected by the sensors. The sensors may be standalone sensors 375, or may be badges 220A-N. Since the badges 220A-N also contain location data, the gas levels displayed on the gas level display 1220 may be updated as the users 120A-N move throughout the workplace.

Figure 13:
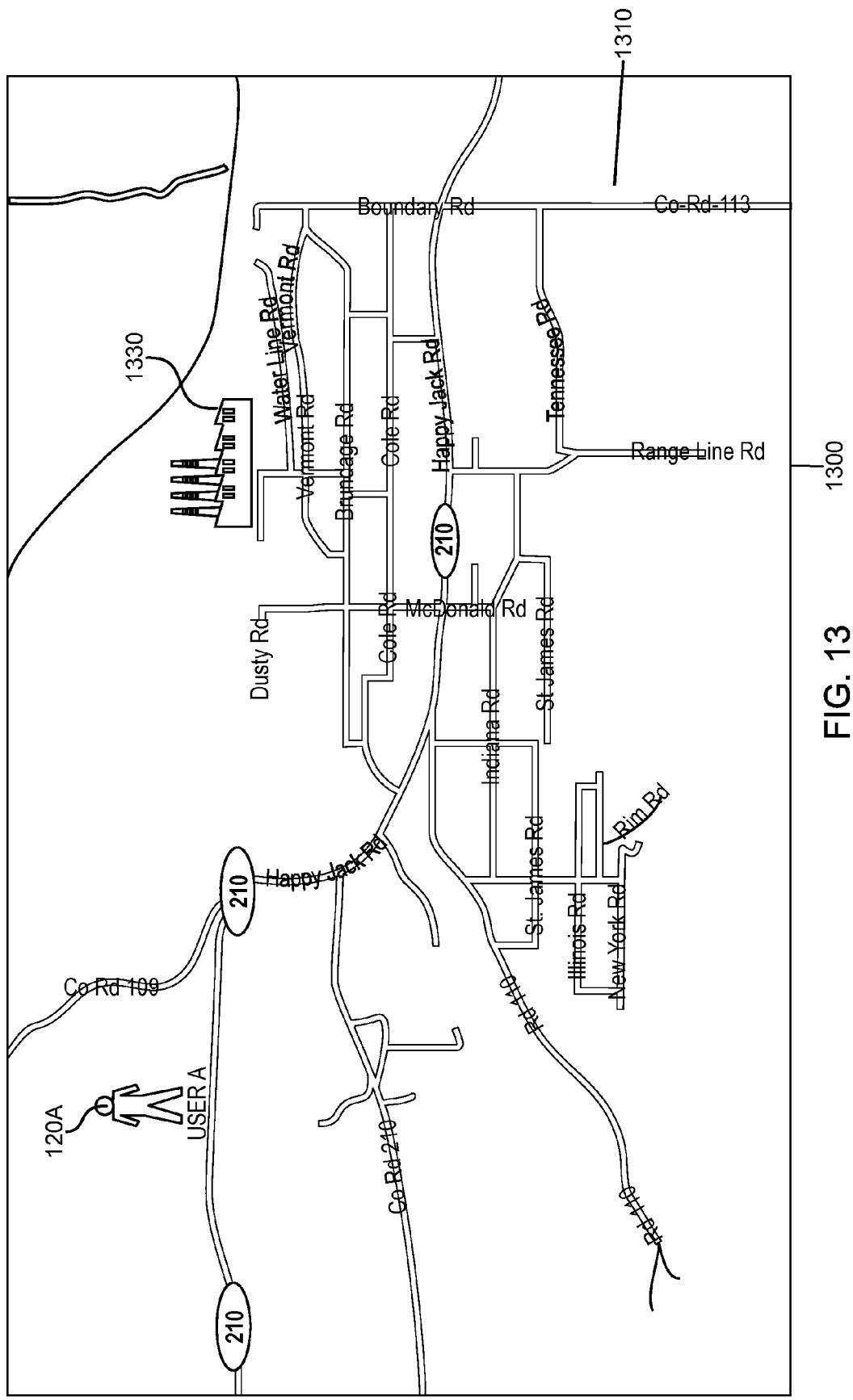
FIG. 13 is a screenshot of a user interface for monitoring the location and gas exposure level of users using a positioning system in the system of FIG. 1, or other systems for providing real time locating and gas exposure monitoring.

FIG. 13 is a screenshot of a user interface 1300 for monitoring the location and gas exposure level of users using a positioning system in the system of FIG. 1, or other systems for providing real time locating and gas exposure monitoring. The user interface 1300 may include a map display 1310, a user A 120A, and a workplace 1330. The user interface 1300 may be provided to the operator 110, such as through the computing device 210.

In operation, the operator 110 may use the map display 1310 to view the location of the users 120A-N outside of the workplace 1330. The users 120A-N may be located remotely from the workplace 1330, or may be located in an area of the workplace outside of the sensor network. The service provider server 240 may utilize positioning data, such as GPS data, received from the gas detection and locating devices 220A-N to identify the geographic location of each of the users 120A-N and assets. Alternatively or in addition, if the user A 120A is located out of range of the positioning system satellites, the service provider server 240 may receive location information from the wireless location server 260, from third party programs or servers, such as GOGGLE LATITUDE™, or from cellular phone towers, such as by triangulating signals of cellular phone towers in communication with the badge 220A of the user A 120A. The map display 1310 may also include one or more metrics related to the user A 120A, such as level of gas exposure, location, biometric information, such as heart rate or blood pressure, or generally any other information which may describe the selected user A 120A or asset. Alternatively or in addition, the user interface 1300 may be used for mustering either thru integrating Lenel or through Exciter use.

Figure 14:
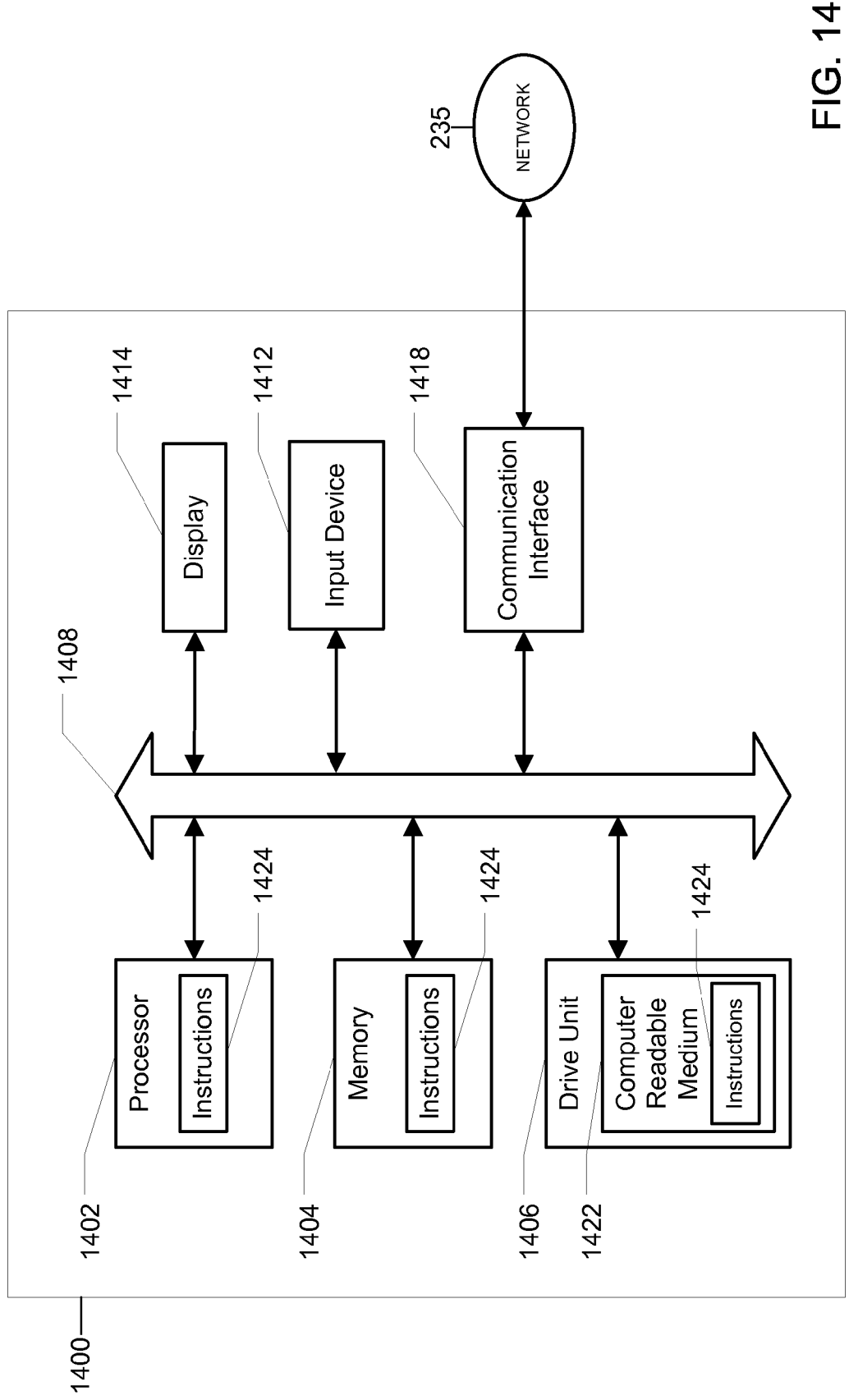
FIG. 14 is an illustration of a general computer system that may be used in the systems of FIG. 2, FIG. 3, or other systems for providing real time locating and gas exposure monitoring.

FIG. 14 illustrates a general computer system 1400, which may represent a service provider server 240, a gas detection and location device 220A-N, 500A, 500B, a computing device 210, a wireless location server 260, a third party server 250, or any of the other computing devices referenced herein. The computer system 1400 may include a set of instructions 1424 that may be executed to cause the computer system 1400 to perform any one or more of the methods or computer based functions disclosed herein. The computer system 1400 may operate as a standalone device or may be connected, e.g., using a network, to other computer systems or peripheral devices.

In a networked deployment, the computer system may operate in the capacity of a server or as a client user computer in a server-client user network environment, or as a peer computer system in a peer-to-peer (or distributed) network environment. The computer system 1400 may also be implemented as or incorporated into various devices, such as a personal computer (PC), a tablet PC, a set-top box (STB), a personal digital assistant (PDA), a mobile device, a palmtop computer, a laptop computer, a desktop computer, a communications device, a wireless telephone, a land-line telephone, a control system, a camera, a scanner, a facsimile machine, a printer, a pager, a personal trusted device, a web appliance, a network router, switch or bridge, or any other machine capable of executing a set of instructions 1424 (sequential or otherwise) that specify actions to be taken by that machine 1n a particular embodiment, the computer system 1400 may be implemented using electronic devices that provide voice, video or data communication. Further, while a single computer system 1400 may be illustrated, the term "system" shall also be taken to include any collection of systems or subsystems that individually or jointly execute a set, or multiple sets, of instructions to perform one or more computer functions.

As illustrated in FIG. 14, the computer system 1400 may include a processor 1402, such as, a central processing unit (CPU), a graphics processing unit (GPU), or both. The processor 1402 may be a component in a variety of systems. For example, the processor 1402 may be part of a standard personal computer or a workstation. The processor 1402 may be one or more general processors, digital signal processors, application specific integrated circuits, field programmable gate arrays, servers, networks, digital circuits, analog circuits, combinations thereof, or other now known or later developed devices for analyzing and processing data. The processor 1402 may implement a software program, such as code generated manually (i.e., programmed).

The computer system 1400 may include a memory 1404 that can communicate via a bus 1408. The memory 1404 may be a main memory, a static memory, or a dynamic memory. The memory 1404 may include, but may not be limited to computer readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one case, the memory 1404 may include a cache or random access memory for the processor 1402. Alternatively or in addition, the memory 1404 may be separate from the processor 1402, such as a cache memory of a processor, the system memory, or other memory. The memory 1404 may be an external storage device or database for storing data. Examples may include a hard drive, compact disc ("CD"), digital video disc ("DVD"), memory card, memory stick, floppy disc, universal serial bus ("USB") memory device, or any other device operative to store data. The memory 1404 may be operable to store instructions 1424 executable by the processor 1402. The functions, acts or tasks illustrated in the figures or described herein may be performed by the programmed processor 1402 executing the instructions 1424 stored in the memory 1404. The functions, acts or tasks may be independent of the particular type of instructions set, storage media, processor or processing strategy and may be performed by software, hardware, integrated circuits, firm-ware, micro-code and the like, operating alone or in combination. Likewise, processing strategies may include multiprocessing, multitasking, parallel processing and the like.

The computer system 1400 may further include a display 1414, such as a liquid crystal display (LCD), an organic light emitting diode (OLED), a flat panel display, a solid state display, a cathode ray tube (CRT), a projector, a printer or other now known or later developed display device for outputting determined information. The display 1414 may act as an interface for the user to see the functioning of the processor 1402, or specifically as an interface with the software stored in the memory 1404 or in the drive unit 1406.

Additionally, the computer system 1400 may include an input device 1412 configured to allow a user to interact with any of the components of system 1400. The input device 1412 may be a number pad, a keyboard, or a cursor control device, such as a mouse, or a joystick, touch screen display, remote control or any other device operative to interact with the system 1400.

The computer system 1400 may also include a disk or optical drive unit 1406. The disk drive unit 1406 may include a computer-readable medium 1422 in which one or more sets of instructions 1424, e.g. software, can be embedded. Further, the instructions 1424 may perform one or more of the methods or logic as described herein. The instructions 1424 may reside completely, or at least partially, within the memory 1404 and/or within the processor 1402 during execution by the computer system 1400. The memory 1404 and the processor 1402 also may include computer-readable media as discussed above.

The present disclosure contemplates a computer-readable medium 1422 that includes instructions 1424 or receives and executes instructions 1424 responsive to a propagated signal; so that a device connected to a network 235 may communicate voice, video, audio, images or any other data over the network 235. Further, the instructions 1424 may be transmitted or received over the network 235 via a communication interface 1418. The communication interface 1418 may be a part of the processor 1402 or may be a separate component. The communication interface 1418 may be created in software or may be a physical connection in hardware. The communication interface 1418 may be configured to connect with a network 235, external media, the display 1414, or any other components in system 1400, or combinations thereof. The connection with the network 235 may be a physical connection, such as a wired Ethernet connection or may be established wirelessly as discussed below. Likewise, the additional connections with other components of the system 1400 may be physical connections or may be established wirelessly. In the case of a service provider server 240, the service provider server may communicate with users 120A-N through the communication interface 1418.

The network 235 may include wired networks, wireless networks, or combinations thereof. The wireless network may be a cellular telephone network, an 802.11, 802.16, 802.20, or WiMax network. Further, the network 235 may be a public network, such as the Internet, a private network, such as an intranet, or combinations thereof, and may utilize a variety of networking protocols now available or later developed including, but not limited to TCP/IP based networking protocols.

The computer-readable medium 1422 may be a single medium, or the computer-readable medium 1422 may be a single medium or multiple media, such as a centralized or distributed database, and/or associated caches and servers that store one or more sets of instructions. The term "computer-readable medium" may also include any medium that may be capable of storing, encoding or carrying a set of instructions for execution by a processor or that may cause a computer system to perform any one or more of the methods or operations disclosed herein.

The computer-readable medium 1422 may include a solid-state memory such as a memory card or other package that houses one or more non-volatile read-only memories. The computer-readable medium 1422 also may be a random access memory or other volatile re-writable memory. Additionally, the computer-readable medium 1422 may include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that may be a tangible storage medium. Accordingly, the disclosure may be considered to include any one or more of a computer-readable medium or a distribution medium and other equivalents and successor media, in which data or instructions may be stored.

Alternatively or in addition, dedicated hardware implementations, such as application specific integrated circuits, programmable logic arrays and other hardware devices, may be constructed to implement one or more of the methods described herein. Applications that may include the apparatus and systems of various embodiments may broadly include a variety of electronic and computer systems. One or more embodiments described herein may implement functions using two or more specific interconnected hardware modules or devices with related control and data signals that may be communicated between and through the modules, or as portions of an application-specific integrated circuit. Accordingly, the present system may encompass software, firmware, and hardware implementations.

The methods described herein may be implemented by software programs executable by a computer system. Further, implementations may include distributed processing, component/object distributed processing, and parallel processing. Alternatively or in addition, virtual computer system processing maybe constructed to implement one or more of the methods or functionality as described herein.

Although components and functions are described that may be implemented in particular embodiments with reference to particular standards and protocols, the components and functions are not limited to such standards and protocols. For example, standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same or similar functions as those disclosed herein are considered equivalents thereof.

The illustrations described herein are intended to provide a general understanding of the structure of various embodiments. The illustrations are not intended to serve as a complete description of all of the elements and features of apparatus, processors, and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

The above disclosed subject matter is to be considered illustrative, and not restrictive, and the appended claims are intended to cover all such modifications, enhancements, and other embodiments, which fall within the true spirit and scope of the description. Thus, to the maximum extent allowed by law, the scope is to be determined by the broadest permissible interpretation of the following claims and their equivalents, and shall not be restricted or limited by the foregoing detailed description.

We claim:

1. A computer-implemented method for providing real time locating and gas exposure monitoring, the method comprising:
   receiving, by a computer processor, a first gas exposure identifier and a first location identifier from a first device;
   identifying a first relative location of the first device based on the first location identifier;
   identifying an amount of gas detected by the first device at the first relative location based on the first gas exposure identifier;
   receiving, by the computer processor, a second location identifier from a second device;
   identifying a second relative location of the second device based on the second location identifier;
   transmitting alert information to the second device when the second relative location is within a predetermined distance from the first relative location and an amount of gas detected by the first device at the first relative location is above a set amount.

2. The computer-implemented method of claim 1 wherein the first device comprises a location device and a gas detector.

3. The computer-implemented method of claim 2 wherein the location device and the gas detector are in communication via a wired connection.

4. The computer-implemented method of claim 2 wherein the location device and the gas detector are in communication via a wireless connection.

5. The computer-implemented method of claim 4 wherein the wireless connection comprises a Bluetooth connection.

6. The computer-implemented method of claim 2 wherein the location device comprises a positioning system.

7. The computer-implemented method of claim 1 further comprising:
   receiving, by the computer processor, a secondary location identifier from a network infrastructure when the first location identifier does not identify a location of the first device, and
   determining a location of the first device based on the secondary location identifier.

8. A computer-implemented method for providing real time locating and gas alert monitoring, the method comprising:
   determining a first location of a first device;
   transmitting to a remote server, by the first device, a location identifier that identifies the first location;

receiving, at the first device, alert information from the remote server when the first location of the first device is within a predetermined distance from a second location where a second device has detected an amount of gas that is above a set amount, and providing, by the first device, an alert on the first device when the alert information is received from the remote server.

9. The computer-implemented method of claim 8 wherein the alert comprises at least one of a vibrating alert, an audible alert, or a visible alert.

10. The computer-implemented method of claim 8 further comprising:

detecting, by the first device, a gas level amount;

transmitting, to the remote server, a gas exposure identifier that identifies the gas level amount detected by the first device;

initiating a communication with a communication device of an emergency responder based on the gas exposure identifier.

11. The computer-implemented method of claim 10 wherein the first device comprises a location device and a gas detector.

12. The computer-implemented method of claim 11 wherein the location device and the gas detector are in communication via a wired connection.

13. The computer-implemented method of claim 11 wherein the location device and the gas detector are in communication via a wireless connection.

14. The computer-implemented method of claim 13 wherein the wireless connection comprises a Bluetooth connection.

15. A system for providing real time locating and gas exposure monitoring, the system comprising:

an interface configured to communicate with a first device, a second device, and a communication device of an emergency responder; and a memory configured to store a first gas exposure identifier and a first location identifier received from the first device via the interface, and a second location identifier received from the second device via the interface, and a processor operatively connected to the memory and the interface, the processor configured to:

receive, via the interface, the first gas identifier, the first location identifier and the second location identifier, identify a first relative location of the first device based on the location identifier, identify an amount of gas detected by the first device at the first relative location based on the first gas exposure identifier, determine whether the amount of gas detected by the first device at the first relative location is above a set amount, identify a second relative location of the second device based on the second location identifier, transmit alert information to the second device when the second relative location is within a predetermined distance from the first relative location and an amount of gas detected by the first device at the first relative location is above a set amount.

16. The system of claim 15 wherein the first device comprises a location device and a gas detector.

17. The system of claim 16 wherein the location device and the gas detector are in communication via a wired connection.

18. The system of claim 16 wherein the location device and the gas detector are in communication via a wireless connection.

19. The system of claim 18 wherein the wireless connection comprises a Bluetooth connection.

20. The system of claim 16 wherein the location device comprises a positioning system.

21. The system of claim 15 wherein the interface is further configured to receive a secondary location identifier from a network infrastructure when the first location identifier does not identify a location of the first device, and the processor is further configured to identify a location of the first device based on the secondary location identifier.

22. The computer-implemented method of claim 1, further comprising:

receiving, by the computer processor, a second gas exposure identifier;

identifying an amount of gas detected by the second device at the second relative location based on the second gas exposure identifier; and initiating a communication with a communication device of an emergency responder based on the gas exposure identifier.

23. The system of claim 15 wherein the interface is further configured to receive a second gas exposure identifier, and the processor is further configured to identify an amount of gas detected by the second device based on the second gas exposure identifier, and initiate a communication with the communication device of the emergency responder based on the second gas exposure identifier.

* * * * *

UNITED STATES PATENT AND TRADEMARK OFFICE
CERTIFICATE OF CORRECTION

PATENT NO. : 8,330,605 B2  
APPLICATION NO. : 12/634110  
DATED : December 11, 2012  
INVENTOR(S) : Johnson et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 450 days.

Signed and Sealed this
Thirtieth Day of April, 2013

Teresa Stanek Rea
*Acting Director of the United States Patent and Trademark Office*